United States Patent
Zhu et al.

(10) Patent No.: US 7,696,407 B2
(45) Date of Patent: *Apr. 13, 2010

(54) PROTEINS AND DNA RELATED TO SALT TOLERANCE IN PLANTS

(75) Inventors: Jian-Kang Zhu, Tucson, AZ (US); Huazhong Shi, Davis, CA (US); Manabu Ishitani, Cary, NC (US); Becky Stevenson, Tucson, AZ (US)

(73) Assignee: The Arizona Board of Regents, Tucson, AZ (US)

( * ) Notice: Subject to any disclaimer, the term of this patent is extended or adjusted under 35 U.S.C. 154(b) by 106 days.

This patent is subject to a terminal disclaimer.

(21) Appl. No.: 10/749,386

(22) Filed: Jan. 2, 2004

(65) Prior Publication Data

US 2004/0186276 A1 Sep. 23, 2004

Related U.S. Application Data

(62) Division of application No. 09/824,734, filed on Apr. 4, 2001, now Pat. No. 6,727,408.

(60) Provisional application No. 60/194,648, filed on Apr. 4, 2000.

(51) Int. Cl.
*C12N 15/82* (2006.01)
(52) U.S. Cl. ........................ 800/278; 800/287
(58) Field of Classification Search ................ 800/278, 800/290, 287
See application file for complete search history.

(56) References Cited

U.S. PATENT DOCUMENTS

| 5,451,514 | A | 9/1995 | Boudet et al. |
| 6,727,408 | B2 * | 4/2004 | Zhu et al. .................. 800/298 |

OTHER PUBLICATIONS

Shi et al (2000, PNAS 97(12):6896-6901).*
Larkin et al (1994, The Plant Cell 6:1065-1076).*
Onouchi et al., 2000, The Plant Cell 12(6):885-900.*
Shi et al (2002, Nature Biotechnology, published online).*
Martinez-Atienza et al (2006, Plant Physiol., Plant Physiology Preview).*
Liu et al (2000, PNAS 97(7):3730-3734).*
Bowie et al, Science 247:1306-1310, 1990.*
McConnell et al, Nature 411 (6838):709-713, 200.*
Fourgoux-Nicol et al. (1999) Plant Molecular Biology 40:857-872.
Lin et al. (Mar. 12, 1999) NCBI Database Accession No. AC006532, Version 3.
Shi et al. (2000) PNAS 97(12):6896-6901.
Larkin et al (1994) The Plant Cell 6:1065-1076.
Bowie et al. (1990) Science 247:1306-10.
.McConnell et al. (2001) Nature 411 (6838):709-713.
Shaw-Jye Wu et al., SOS1, A Genetic Locus Essential for Salt Tolerance and Potassium Acquisition, The Plant Cell, vol. 8, pp. 617-627, Apr. 1996.

* cited by examiner

*Primary Examiner*—Stuart F. Baum
(74) *Attorney, Agent, or Firm*—Oblon, Spivak, McClelland, Maier & Neustadt, L.L.P.

(57) ABSTRACT

The present invention relates to proteins and nucleic acids related to salt tolerance in plants.

13 Claims, 11 Drawing Sheets

FIG. 3A

```
MTTVIDATMAYRFLEEATDSSSSSSKLESSPVDAVLFVGMSLVLGIAS
RHLLRGTRVPYTVALLVIGIALGSLEYGAKHNLGKIGHGIRIWNEIDPEL
                            TM1
LLAVELPALLFESSFSMEVHQIKRCLGQMVLLAVPGVLISTACLGSLVKV
         TM2
TFPYEWDWKTSLLLGGLLSATDPVAVVALLKELGASKKLSTIIEGESLMN
     TM3                      TM4
DGTAIVVFQLFLKMAMGQNSDWSSIIKFLLKVALGAVGIGLAFGIASVIW
                     TM5
LKFIFNDTVIEITLTIAVSFAYYTAQEWAGASGVLTVMTLGMFYAAFAR
       TM6                          TM7
TAFKGDSQKSLHHFWEMVAYIANTLIFILSGVVIAEGILDSDKIAYQGNS
                                TM8
WRFLFLLYVYIQLSRVVVVGVLYPLLCREGYGLDWKESIILVWSGLRGAV
                           TM9
ALALSLSVKQSSGNSHISKETGTLFLFFTGGIVFLTLIVNGSTTQFVLRL
          TM10
LRMDILPAPKKRILEYTKYEMLNKALRAFQDLGDDEELGPADWPTVESYI
  TM11                      TM12
SSLKGSEGELVHHPHNGSKIGSLDPKSLKDIRMRFLNGVQATYWEMLDEG
RISEVTANILMQSVDEALDQVSTTLCDWRGLKPHVNFPNYYNFLHSKVVP
RKLVTYFAVERLESACYISAAFLRAHTIARQQLYDFLGESNIGSIVINES
EKEGEEAKKFLEKVRSSFPQVLRVVKTKQVTYSVLNHLLGYIENLEKVGL
LEEKEIAHLHDAVQTGLKKLLRNPPIVKLPKLSDMITSHPLSVALPPAFC
EPLKHSKKEPMKLRGVTLYKEGSKPTGVWLIFDGIVKWKSKILSNNHSLH
PTFSHGSTLGLYEVLTGKPYLCDLITDSMVLCFFIDSEKILSLQSDSTID
DFLWQESALVLLKLLRPQIFESVAMQELRALVSTESSKLTTYVTGESIEI
DCNSIGLLLEGFVKPVGIKEELISSPAALSPSNGNQSFHNSSEASGIMRV
SFSQQATQYIVETRARAIIFNIGAFGADRTLHRRPSSLTPPRSSSSDQLQ
RSFRKEHRGLMSWPENIYAKQQQEINKTTLSLSERAMQLSIFGSMVNVYR
RSVSFGGIYNNKLQDNLLYKKLPLNPAQGLVSAKSESSIVTKKQLETRKH
ACQLPLKGESSTRQNTMVESSDEEDEDEGIVVRIDSPSKIVFRNDL
```

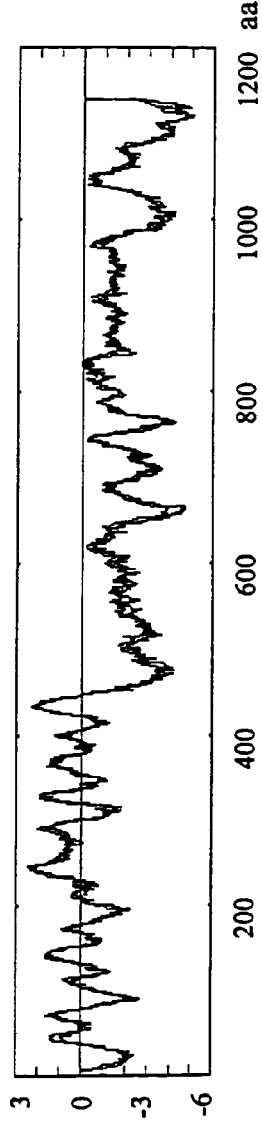

```
SOS1    1   MTTVIDATMAYRFLEEATDSSSSSSSSKLESSPVDAVLFVGMSLVLGLASRHLLRGTRV
NhaP    1                              MLDLVAAFLALLLLTYVN---YRFTRL
NHE1   61   VTTAPSEPVHHPDDRNLTNLHIEHGAKTLRKAFPVLDLDYLHVRLPFEISLWILLACLMK

SOS1   60   PYDVAILVICIALGSLEYGAKHN---LGKIGHGIRIWNELDPELLAVFLPALLFESSES
NhaP   26   PPTLGMLATALVFSLLVQGLSELGYPLLELEMQEILRRIDFSEVLLTLFLPALLFAGALH
NHE1  121   IGFHVLPTISSLVPESCLLLVVGLLVGGLIKGVGETPPFLQSDVFFLLLPPLLLDAGYF

SOS1  117   LEVHQLKRCLGQVLLAVPGVLISTACLGSLLKVTFP------YEWDLKTSLLLGGLLSA
NhaP   86   VDLSDLRSYKWPLGLLATAGVLIATFVLGGLAYYTFPLFG---WQLDELYCLLFGALISP
NHE1  181   LPLRQFTENLGTILLFAVVGTLWNAFLGGLLYAVCLVGGEQINLLGLLDILLFGSLISA

SOS1  171   TDPVAVVALLKELGASKKLSTLIEGESLMNDGTALVVFQLFL-KLAMGQN--SDWSSIIK
NhaP  143   TDPLAVLGLLKSAGAPKPLATTIVGESLFNDGTAVVVFALILGILLGEA--PTVSATAL
NHE1  241   VDPVAVVALFEELHINELLHILVFGESLLNDAVTVVLYHLFEEFALYDSIGISDLFLGFL

SOS1  228   FLLKVALGLVGIGLALEGLASVIWEKFIFNDTVIELTLTLLMSYFAYYTLQEWAGLSGVLT
NhaP  201   LLVQEALGGVVFGAVLGYGVFLMRGID-QYQWEVLLTLLALVIGGAALAARLMVSAPIAM
NHE1  301   SFFVALGGVFLGLVVGVIAAFTSRFTSHIRVIEPLFVFLYSYMAYLSAELFHLSG-IVA

SOS1  288   VLTLGLFYAAFLASTAFKGLSQLSLHHFWEMLAYLANTLIFILSGVVLAEGILDSDKLAYQ
NhaP  260   VVAGLLTGNHGRLYALLSDLTRRYVDLFWELLIDEILLNALLFALIGLELLLLPFSVLHVAA-
NHE1  360   LLASGLVLMRPLVEANLSHKSLTLLRYFLKMWSSVSETLIFIFLGVSTVAGSHQWN-----

SOS1  348   GNSLRELFLLYVVLQLLSRVVLVGVLYPLLCRFGYLLDWKES---ILLVWLSGLRGAVALAL
NhaP  319   --A--FALLG--GAVLLSRLLTVGPAILVLRRFFGANRQVPAGTIRILVWGGLRGGVSVAL
NHE1  415   ---VTFLVSTLLLCLLARVLGVLVLTWFINKFRIVKLTPKDQ--FILAYGGLRGAILFSL

SOS1  405   SLSLKQS--SGNSHLSKELGTLLFLL--FTGGLVFLTLLVNGSTTQFVLRL
NhaP  373   ALSLPLG--EERDLILSLTYIVVLVSLLLQGLSLGPLVRRLYAGQPLLEKS
NHE1  470   GYLLDKKHFLMCDLFLLAIITVFFFTVFVQGLTIRPLVDLLAVKKKQLTK
```

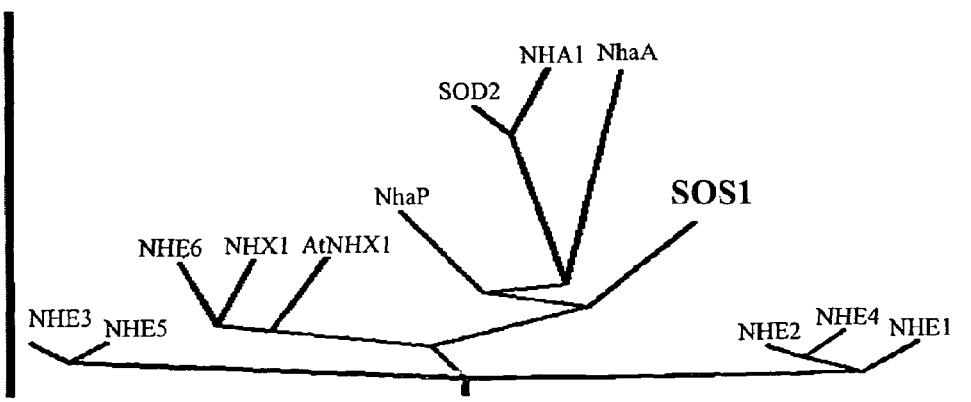

FIG. 4B

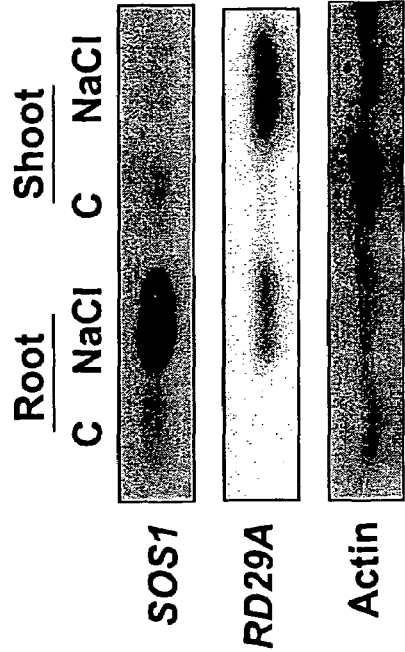
FIG. 6C
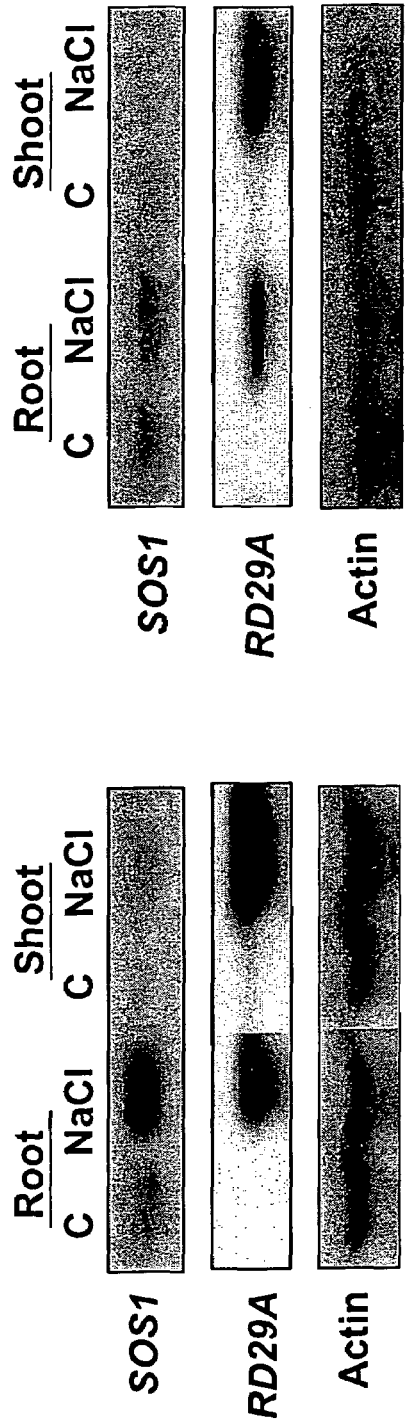
FIG. 6D
FIG. 6A
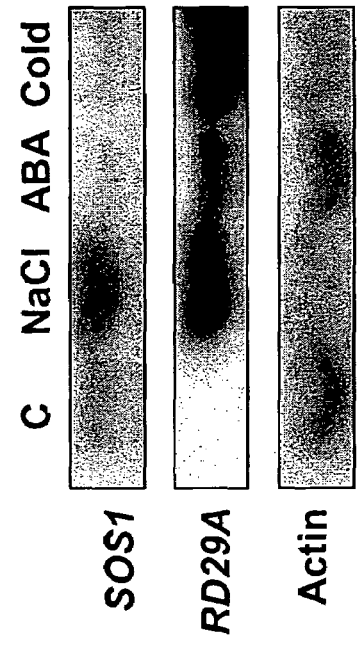
FIG. 6B 1 atgacgactg taatcgacgc gacgatggcg tatagatttc tggaggaagc gaccgattcg
61 tcttcttctt cttcttcttc caaactagaa tctagccctg tcgacgccgt tctcttcgtc
121 ggaatgtctc tggtactcgg tattgcttct aggcacttgc ttcgtggaac tagggttcct
181 tacactgtcg ctcttctcgt tatcggaatt gctcttggat ctctcggttc gatttcgttc
241 catggaattt ctgatttctt catctgtttt aatccttgaa gtcaacgtaa tcatgcttaa
301 ttgctaattc atgttgtttg gtgtttcaga atatggagct aaacataacc ttggaaagat
361 cggccatgga attcgtatct gtaagttttt agtttcgaat ttttcttctc ttccatggct
421 ggctttgtaa gaactataga atcaatgtta ttgtgcaggg aatgagatcg atccagaact
481 tcttttagct gtttttcttc cggctcttct tttcgagagt tcgttttcaa tggaagttca
541 ccaaattaag gtttattcct ctggctctaa ttcctagtta agcttaaagg ttaagagaaa
601 taggtactga atacttgcat gattctttag aggtgtctgg gacaaatggt gttacttgct
661 gtccctggag ttcttatttc aacagcttgt cttggatcgc ttgtgaaggt atgaattagc
721 ctggttggta ttaagtagct gtcctgaaaa caaagaaaga caaatcgatt attatgttat
781 gaaactatac ttgctatatg caggtcacgt ttccgtatga atgggactgg aaaacgtcct
841 tgttgcttgg gggacttta agtgctactg atccggttgc tgttgttgct ttgctaaagg
901 agcttggtgc tagtaagaag ctaagcacca taattgaagg ggaatccctg atgaatgatg
961 ggtaaatgac gttatcttct gtcatggttt ggttagtttt gacatttatg ctcactcttc
1021 atgattttta acaacaattc caggacggcg attgttgttt tccagttatt cttaaagatg
1081 gctatggggc aaaactctga ctggagttct ataatcaaat ttctgcttaa agtcgcactt
1141 ggagcgtatg tcttgatctt ttttcatctg ttgttagtga tatcaagttg ctgctgtgtt
1201 cttatcagtc caacgtgttc ttctgtctat ttagtgtagg cattggtctg gcgtttggca
1261 ttgcatcagt tatttggctc aagttcatat tcaatgacac tgtaatagag attactctta
1321 caattgcagt gagctatttc gcatactaca ctgtacgtct ttctgtagac cttgaattcc
1381 tgtgctaaga tattctcttt gtagtaaaac tgagagttta ttgtgtgaca ggctcaagag
1441 tgggctgggg cttctggtgt tttgacggtc atgactttgg gcatgtaaat ttcagtgatc
1501 tcgttatttt ttttttcccct ttcttttgtt atcatttaag aagtctcttc tcataaaata
1561 actgtaacag gtttatgct gcatttgcaa ggacagcctt taaaggtgac agtcaaaaaa
1621 gcttgcatca cttctggtat ttccagaact tgtggaattt ggacttgttt ttttatattg
1681 taactctatg taaaaggttg atctgtgtga tataaatttt cccggtaact tgtgcaggga
1741 aatggttgca tatattgcaa acactttgat atttatcctc aggtaagggt aaatttata
1801 gactcatatc atgcttgtgc ttgccaaccc taaaatagaa gctcatgggt agaaaaaaga
1861 gctatttac tgcagtctac tctttagcct ggtgttgcaa tattgactgt gtttctcgtt
1921 ttatgtttgc agtggtgttg tcattgctga aggcattctc gacagtgata agattgccta

*FIG. 7A*

1981 ccaaggtgcc attatttaat gttgatagtg tacagtattt ttttcctagc taaagtaaat
2041 tttgtgaaca tagttttgtc tgcattttcg acagttcact gttaattgaa gatgagatct
2101 aagtcattac ataggactcc cacctgttat catagttttc tgtcgttgtt aacacaccft
2161 actgttcatg gtctttggtt ctcgaaggat cactaattcc ataacgtgaa tcagttacaa
2221 gaataagaaa aaaactggca ttattggtta cgaaatattg agcgaaagtt accactgtgc
2281 taggactgag acaattgtat tctttcacca gtctgttatt attattaagt acctgttaga
2341 gatgtactgt cttggaacca tatattttt ctctggaacc atatctgcat aaggcacatg
2401 atatacttaa ctttaactat tttttatatt ttggatctaa caactcttca cgacccaaat
2461 ttcttacagg gaattcatgg cgatttcttt ttctgctata cgtttacatc caactatcgc
2521 gtgttgttgt tgttggagtt ctatatccac ttttatgtcg ttttggctat ggtttggatt
2581 ggaaagaatc cattatactc gtatggtctg gtttgagggg cgcagtggct cttgcacttt
2641 ctttatccgt gaaggttaat tttaagaaca tctgttaaag ttgttcttct ctcttaaatt
2701 tctgcacaat gttttttcc agccacattg attctgtgct gacttactcg cactcatttg
2761 attcagcaat caagcggaaa ttcacatatc agcaaggaga ctggaacatt ggtaagttag
2821 tctaaagatg ttattgacaa cttaaaatga ttatgcaaat tattgttttg tctcttcata
2881 ttctcagttc ttttgcagtt tcttttcttc acgggtggaa ttgtgttcct aactctgata
2941 gttaatggat ccactaccca atttgttcta cgccttcttc gcatggatat tttaccagcc
3001 cccaaggtca aaaacttctc tcatacgaat aactttccga gttttaagta atcaaatata
3061 tgtgtaaaca gagattttt tgcttatgct ttgtattcat gtgtaagtga ccgtgttagc
3121 ctgagtctga gcctttaagc tgtatagttc aatagggtct gtatgttcta gtcagtaatg
3181 tattcgaaga accttattag aaaccactt ccttttgaca gaaacgaata ttggaatata
3241 caaagtacga aatgttgaat aaggccttac gagcgtttca agatctagga gacgatgagg
3301 agctaggacc tgctgactgg cctacagttg aaagttatat ttcaagccta aaaggttcag
3361 aaggggaact agttcatcat cctcacaatg gctctaaaat tggaagtctt gaccctaaaa
3421 gtttaaagga catacgtatg cggttcttaa atggtagtta tgatcatgta cctccaata
3481 tactatttta cctggtagat tattgacact ttgaaaattg gttgtgtcag gtgtgcaagc
3541 aacttactgg gagatgcttg atgagggcag aatatctgaa gttactgcta atattttgat
3601 gcagtcagtg gatgaggcgc ttgatcaggt ttctacaact ttatgtgatt ggagaggtct
3661 aaaaccacat gtcaatttcc caaattacta caactttctt cattctaaag ttgtcccacg
3721 caagttggtc acatactttg ctgtcgaaag actagaatct gcttgctaca tttctgctgc
3781 gtttcttcgc gcacatacaa ttgcacgaca gcaattgtat gattttctag gtatgtacaa
3841 tccatactct gcagtctgca tcacactttg aaaacaatga ctaagaataa aacttgtacc
3901 gtatcatcat taattgtcag agtttttgtt tgcaagtatc tcaacttagt aagaacaata
3961 cattaaccca accctagttt tgtctcatac ttatctatct tctctacaca ggggagagta

*FIG. 7B*

4021 atattggttc cattgtaatc aatgaaagtg aaaaggaagg agaggaagca aaaaagttct
4081 tggaaaaagt ccgatcttca tttcctcagg ttgagagtct tgtcatttct ttcgggtgac
4141 ttatcttct tgcggtgagg cacatataat ctttgattaa cattggtttc aggttctccg
4201 tgttgtgaaa acaaaacaag taacatattc agtgttgaat catttactcg gttacattga
4261 aaacctcgag aaggttggct tgttggagga aaaagaaatc gctcatcttc atgatgctgt
4321 ccaggtacca aattaaagaa tctcattcct tcaactatag tcttgtctct tttgtcttat
4381 gcttttggtc aaatctatct ctgcagaccg gcttgaaaaa gcttttgaga aaccctccaa
4441 tagttaaact tccaaaattg agcgacatga tcacctcaca tccgttatcg gttgctcttc
4501 ctcctgcatt ttgtgaacct ttaaaacact cgaaaaaaga accaatgaaa ctgcgtggtg
4561 tcacgcttta taagaaggt tcaaagccaa ctggagtctg gcttatttt gatggcatcg
4621 ttaaggtaac ccaaaactta tcttttactt ttaactcgta agtctgtatg atctattacc
4681 ttcataactg aatgttataa caatcctaca gtggaaaagt aagatcttaa gcaacaatca
4741 ctcgctgcat ccaactttt ctcacggtag tacattggga ctctacgaag tcctcactgg
4801 gaagccatat ctgtgcgact tgattacaga ttctatggtt ctttgctttt tcattgatag
4861 cgagaaaatt ctatcactac aatcagattc taccatcgat gatttccttt ggcaggtacg
4921 tctctattag aatccatttt agagagactc atttcttgat tgttaagttg cttcaacttt
4981 tttcggtttt ttttgtttgc aggaaagtgc attggttctt ctcaaactct tgcgtcctca
5041 gatatttgaa agtgtggcaa tgcaagaatt acgagccctt gtttcaactg aaagctcgaa
5101 acttacaaca tatgtgacgg gagaatcaat cgaaatcgac tgcaacagca ttggtttatt
5161 attagaagga ttcgtaaaac cggttggtat caaagaagag cttatatcat ctcccgccgc
5221 attatcacct tctaacggga atcaaagctt ccataattca tcagaagctt caggtaatta
5281 attgcacagt acagcaggat caaacctttt taaatgtcag cgaatgatat aaatcgaatt
5341 aaatcaaaaa tgtgttttgt ttttttgacc acaggtatca tgagagtcag tttctcacaa
5401 caagcaacac agtatattgt tgagacgaga gcaagagcaa tcatcttcaa cattggagca
5461 tttggagctg ataggactct acatcgaaga ccatcttcgt taacaccacc acgtagctca
5521 agctctgatc agcttcagag atcatttcgt aaagaacaca gaggtctcat gagctggcct
5581 gaaaatattt acgccaaaca acaacaagag atcaataaaa cgacattaag tttatctgaa
5641 cgagcaatgc aactcagcat tttcggcagc atggtaaaaa agatctcaat gttgattctt
5701 ttaaaggttg ttatcgatga acttctcgac taacctgaag gtttttatct tctgatattc
5761 tcgaatatag gttaatgtgt acagaaggag tgtaagtttc ggtgggatct ataataacaa
5821 gttacaagat aacttgttgt acaaaaaact tccactaaac ccagctcaag gtctcgtttc
5881 agccaaatca gaaagttcaa ttgtgaccaa gaagcagctt gaaacccgta acatgcgtg
5941 tcagcttcct ctgaaagggg aaagcagcac aaggcaaaat acgatggttg aatcaagcga
6001 tgaagaagat gaagatgaag gaatcgttgt gagaatcgat tctccgagta aaatcgtttt

FIG. 7C

6061 caggaacgat ctatga

*FIG. 7D*

SEQUENCE LISTING

```
<160> NUMBER OF SEQ ID NOS: 20

<210> SEQ ID NO 1
<211> LENGTH: 6076
<212> TYPE: DNA
<213> ORGANISM: Arabidopsis thaliana
<220> FEATURE:
<221> NAME/KEY: CDS
<222> LOCATION: (1)..(226)
<223> OTHER INFORMATION:
<220> FEATURE:
<221> NAME/KEY: CDS
<222> LOCATION: (330)..(380)
<223> OTHER INFORMATION:
<220> FEATURE:
<221> NAME/KEY: CDS
<222> LOCATION: (459)..(550)
<223> OTHER INFORMATION:
<220> FEATURE:
<221> NAME/KEY: CDS
<222> LOCATION: (631)..(708)
<223> OTHER INFORMATION:
<220> FEATURE:
<221> NAME/KEY: CDS
<222> LOCATION: (804)..(961)
<223> OTHER INFORMATION:
<220> FEATURE:
<221> NAME/KEY: CDS
<222> LOCATION: (1044)..(1145)
<223> OTHER INFORMATION:
<220> FEATURE:
<221> NAME/KEY: CDS
<222> LOCATION: (1235)..(1352)
<223> OTHER INFORMATION:
<220> FEATURE:
<221> NAME/KEY: CDS
<222> LOCATION: (1432)..(1484)
<223> OTHER INFORMATION:
<220> FEATURE:
<221> NAME/KEY: CDS
<222> LOCATION: (1571)..(1636)
<223> OTHER INFORMATION:
<220> FEATURE:
<221> NAME/KEY: CDS
<222> LOCATION: (1738)..(1782)
<223> OTHER INFORMATION:
<220> FEATURE:
<221> NAME/KEY: CDS
<222> LOCATION: (1933)..(1985)
<223> OTHER INFORMATION:
<220> FEATURE:
<221> NAME/KEY: CDS
<222> LOCATION: (2470)..(2654)
<223> OTHER INFORMATION:
<220> FEATURE:
<221> NAME/KEY: CDS
<222> LOCATION: (2767)..(2811)
```

```
<223> OTHER INFORMATION:
<220> FEATURE:
<221> NAME/KEY: CDS
<222> LOCATION: (2899)..(3006)
<223> OTHER INFORMATION:
<220> FEATURE:
<221> NAME/KEY: CDS
<222> LOCATION: (3222)..(3453)
<223> OTHER INFORMATION:
<220> FEATURE:
<221> NAME/KEY: CDS
<222> LOCATION: (3531)..(3830)
<223> OTHER INFORMATION:
<220> FEATURE:
<221> NAME/KEY: CDS
<222> LOCATION: (4012)..(4109)
<223> OTHER INFORMATION:
<220> FEATURE:
<221> NAME/KEY: CDS
<222> LOCATION: (4193)..(4324)
<223> OTHER INFORMATION:
<220> FEATURE:
<221> NAME/KEY: CDS
<222> LOCATION: (4407)..(4625)
<223> OTHER INFORMATION:
<220> FEATURE:
<221> NAME/KEY: CDS
<222> LOCATION: (4712)..(4915)
<223> OTHER INFORMATION:
<220> FEATURE:
<221> NAME/KEY: CDS
<222> LOCATION: (5003)..(5273)
<223> OTHER INFORMATION:
<220> FEATURE:
<221> NAME/KEY: CDS
<222> LOCATION: (5375)..(5673)
<223> OTHER INFORMATION:
<220> FEATURE:
<221> NAME/KEY: CDS
<222> LOCATION: (5771)..(6073)
<223> OTHER INFORMATION:

<400> SEQUENCE: 1 atg acg act gta atc gac gcg acg atg gcg tat aga ttt ctg gag gaa      48
Met Thr Thr Val Ile Asp Ala Thr Met Ala Tyr Arg Phe Leu Glu Glu
1               5                   10                  15 gcg acc gat tcg tct tct tct tct tct tcc aaa cta gaa tct agc          96
Ala Thr Asp Ser Ser Ser Ser Ser Ser Ser Lys Leu Glu Ser Ser
            20                  25                  30 cct gtc gac gcc gtt ctc ttc gtc gga atg tct ctg gta ctc ggt att     144
Pro Val Asp Ala Val Leu Phe Val Gly Met Ser Leu Val Leu Gly Ile
        35                  40                  45 gct tct agg cac ttg ctt cgt gga act agg gtt cct tac act gtc gct    192
Ala Ser Arg His Leu Leu Arg Gly Thr Arg Val Pro Tyr Thr Val Ala
    50                  55                  60 ctt ctc gtt atc gga att gct ctt gga tct ctc g gttcgatttc           236
Leu Leu Val Ile Gly Ile Ala Leu Gly Ser Leu
65                  70                  75 gttccatgga atttctgatt tcttcatctg ttttaatcct tgaagtcaac gtaatcatgc   296
ttaattgcta attcatgttg tttggtgttt cag aa tat gga gct aaa cat aac    349
                                        Glu Tyr Gly Ala Lys His Asn
                                                            80 ctt gga aag atc ggc cat gga att cgt atc t gtaagttttt agtttcgaat    400
Leu Gly Lys Ile Gly His Gly Ile Arg Ile
            85                  90 ttttcttctc ttccatggct ggctttgtaa gaactataga atcaatgtta ttgtgcag    458 gg aat gag atc gat cca gaa ctt ctt tta gct gtt ttt ctt ccg gct    505
Trp Asn Glu Ile Asp Pro Glu Leu Leu Leu Ala Val Phe Leu Pro Ala
         95                 100                 105
```

-continued

```
ctt ctt ttc gag agt tcg ttt tca atg gaa gtt cac caa att aag         550
Leu Leu Phe Glu Ser Ser Phe Ser Met Glu Val His Gln Ile Lys
    110             115                 120 gtttattcct ctggctctaa ttcctagtta agcttaaagg ttaagagaaa taggtactga    610
atacttgcat gattctttag agg tgt ctg gga caa atg gtg tta ctt gct gtc   663
                         Arg Cys Leu Gly Gln Met Val Leu Leu Ala Val
                             125                 130 cct gga gtt ctt att tca aca gct tgt ctt gga tcg ctt gtg aag         708
Pro Gly Val Leu Ile Ser Thr Ala Cys Leu Gly Ser Leu Val Lys
135             140                 145 gtatgaatta gcctggttgg tattaagtag ctgtcctgaa acaaagaaa gacaaatcga    768 ttattatgtt atgaaactat acttgctata tgcag gtc acg ttt ccg tat gaa     821
                                       Val Thr Phe Pro Tyr Glu
                                           150             155 tgg gac tgg aaa acg tcc ttg ttg ctt ggg gga ctt tta agt gct act     869
Trp Asp Trp Lys Thr Ser Leu Leu Leu Gly Gly Leu Leu Ser Ala Thr
            160                 165                 170 gat ccg gtt gct gtt gtt gct ttg cta aag gag ctt ggt gct agt aag     917
Asp Pro Val Ala Val Val Ala Leu Leu Lys Glu Leu Gly Ala Ser Lys
    175                 180                 185 aag cta agc acc ata att gaa ggg gaa tcc ctg atg aat gat gg          961
Lys Leu Ser Thr Ile Ile Glu Gly Glu Ser Leu Met Asn Asp Gly
    190                 195                 200 gtaaatgacg ttatcttctg tcatggtttg gttagttttg acatttatgc tcactcttca  1021 tgattttta caacaattcc ag g acg gcg att gtt gtt ttc cag tta ttc      1071
                         Thr Ala Ile Val Val Phe Gln Leu Phe
                                 205                 210 tta aag atg gct atg ggg caa aac tct gac tgg agt tct ata atc aaa    1119
Leu Lys Met Ala Met Gly Gln Asn Ser Asp Trp Ser Ser Ile Ile Lys
            215                 220                 225 ttt ctg ctt aaa gtc gca ctt gga gc  gtatgtcttg atcttttttc          1165
Phe Leu Leu Lys Val Ala Leu Gly Ala
        230                 235 atctgttgtt agtgatatca agttgctgct gtgttcttat cagtccaacg tgttcttctg  1225 tctatttag t gta ggc att ggt ctg gcg ttt ggc att gca tca gtt att    1274
             Val Gly Ile Gly Leu Ala Phe Gly Ile Ala Ser Val Ile
                 240                 245 tgg ctc aag ttc ata ttc aat gac act gta ata gag att act ctt aca    1322
Trp Leu Lys Phe Ile Phe Asn Asp Thr Val Ile Glu Ile Thr Leu Thr
250             255                 260                 265 att gca gtg agc tat ttc gca tac tac act gtacgtcttt ctgtagacct      1372
Ile Ala Val Ser Tyr Phe Ala Tyr Tyr Thr
                270                 275 tgaattcctg tgctaagata ttctctttgt agtaaaactg agagtttatt gtgtgacag   1431 gct caa gag tgg gct ggg gct tct ggt gtt ttg acg tca atg act ttg    1479
Ala Gln Glu Trp Ala Gly Ala Ser Gly Val Leu Thr Val Met Thr Leu
        280                 285                 290 ggc at  gtaaatttca gtgatctcgt tattttttt tcccttttct tttgttatca      1534
Gly Met tttaagaagt ctcttctcat aaaataactg taacag g ttt tat gct gca ttt gca  1589
                                         Phe Tyr Ala Ala Phe Ala
                                                     295 agg aca gcc ttt aaa ggt gac agt caa aaa agc ttg cat cac ttc tg     1636
Arg Thr Ala Phe Lys Gly Asp Ser Gln Lys Ser Leu His His Phe Trp
300                 305                 310 gtatttccag aacttgtgga atttggactt gttttttat attgtaactc tatgtaaaag  1696
```

-continued

| | |
|---|---|
| gttgatctgt gtgatataaa ttttcccggt aacttgtgca g g gaa atg gtt gca<br>                                                                                                   Glu Met Val Ala | 1750 |
| tat att gca aac act ttg ata ttt atc ctc ag gtaagggtaa attttataga<br>Tyr Ile Ala Asn Thr Leu Ile Phe Ile Leu Ser<br>320                  325 | 1802 |
| ctcatatcat gcttgtgctt gccaacccta aaatagaagc tcatgggtag aaaaaagagc | 1862 |
| tattttactg cagtctactc tttagcctgg tgttgcaata ttgactgtgt ttctcgtttt | 1922 |
| atgtttgcag t ggt gtt gtc att gct gaa ggc att ctc gac agt gat aag<br>               Gly Val Val Ile Ala Glu Gly Ile Leu Asp Ser Asp Lys<br>                              335                           340 | 1972 |
| att gcc tac caa g gtgccattat ttaatgttga tagtgtacag tatttttttc<br>Ile Ala Tyr Gln<br>    345 | 2025 |
| ctagctaaag taaattttgt gaacatagtt ttgtctgcat tttcgacagt tcactgttaa | 2085 |
| ttgaagatga gatctaagtc attacatagg actcccacct gttatcatag ttttctgtcg | 2145 |
| ttgttaacac accttactgt tcatggtctt tggttctcga aggatcacta attccataac | 2205 |
| gtgaatcagt tacaagaata agaaaaaaac tggcattatt ggttacgaaa tattgagcga | 2265 |
| aagttaccac tgtgctagga ctgagacaat tgtattcttt caccagtctg ttattattat | 2325 |
| taagtacctg ttagagatgt actgtcttgg aaccatatat ttttctctg gaaccatatc | 2385 |
| tgcataaggc acatgatata cttaacttta actattttt atttttgga tctaacaact | 2445 |
| cttcacgacc caaatttctt acag gg aat tca tgg cga ttt ctt ttt ctg<br>                                     Gly Asn Ser Trp Arg Phe Leu Phe Leu<br>                                           350                          355 | 2495 |
| cta tac gtt tac atc caa cta tcg cgt gtt gtt gtt gtt gga gtt cta<br>Leu Tyr Val Tyr Ile Gln Leu Ser Arg Val Val Val Val Gly Val Leu<br>                      360                           365                           370 | 2543 |
| tat cca ctt tta tgt cgt ttt ggc tat ggt ttg gat tgg aaa gaa tcc<br>Tyr Pro Leu Leu Cys Arg Phe Gly Tyr Gly Leu Asp Trp Lys Glu Ser<br>                375                           380                           385 | 2591 |
| att ata ctc gta tgg tct ggt ttg agg ggc gca gtg gct ctt gca ctt<br>Ile Ile Leu Val Trp Ser Gly Leu Arg Gly Ala Val Ala Leu Ala Leu<br>            390                           395                           400 | 2639 |
| tct tta tcc gtg aag gttaatttta agaacatctg ttaaagttgt tcttctctct<br>Ser Leu Ser Val Lys<br>405 | 2694 |
| taaatttctg cacaatgttt ttttccagcc acattgattc tgtgctgact tactcgcact | 2754 |
| catttgattc ag caa tca agc gga aat tca cat atc agc aag gag act gga<br>                Gln Ser Ser Gly Asn Ser His Ile Ser Lys Glu Thr Gly<br>                            410                           415                          420 | 2805 |
| aca ttg gtaagttagt ctaaagatgt tattgacaac ttaaatgat tatgcaaatt<br>Thr Leu | 2861 |
| attgttttgt ctcttcatat tctcagttct tttgcag ttt ctt ttc ttc acg ggt<br>                                               Phe Leu Phe Phe Thr Gly<br>                                                425                           430 | 2916 |
| gga att gtg ttc cta act ctg ata gtt aat gga tcc act acc caa ttt<br>Gly Ile Val Phe Leu Thr Leu Ile Val Asn Gly Ser Thr Thr Gln Phe<br>                     435                           440                           445 | 2964 |
| gtt cta cgc ctt ctt cgc atg gat att tta cca gcc ccc aag<br>Val Leu Arg Leu Leu Arg Met Asp Ile Leu Pro Ala Pro Lys<br>            450                           455                           460 | 3006 |
| gtcaaaaact tctctcatac gaataacttt ccgagtttta agtaatcaaa tatatgtgta | 3066 |
| aacagagatt ttttgctta tgctttgtat tcatgtgtaa gtgaccgtgt tagcctgagt | 3126 |

```
                                                                                          -continued ctgagccttt aagctgtata gttcaatagg gtctgtatgt tctagtcagt aatgtattcg          3186
aagaacctta ttagaaacca ctttccttt gacag aaa cga ata ttg gaa tat             3239
                                      Lys Arg Ile Leu Glu Tyr
                                                           465 aca aag tac gaa atg ttg aat aag gcc tta cga gcg ttt caa gat cta           3287
Thr Lys Tyr Glu Met Leu Asn Lys Ala Leu Arg Ala Phe Gln Asp Leu
            470                 475                 480 gga gac gat gag gag cta gga cct gct gac tgg cct aca gtt gaa agt           3335
Gly Asp Asp Glu Glu Leu Gly Pro Ala Asp Trp Pro Thr Val Glu Ser
                485                 490                 495 tat att tca agc cta aaa ggt tca gaa ggg gaa cta gtt cat cat cct           3383
Tyr Ile Ser Ser Leu Lys Gly Ser Glu Gly Glu Leu Val His His Pro
            500                 505                 510 cac aat ggc tct aaa att gga agt ctt gac cct aaa agt tta aag gac           3431
His Asn Gly Ser Lys Ile Gly Ser Leu Asp Pro Lys Ser Leu Lys Asp
515                 520                 525                 530 ata cgt atg cgg ttc tta aat g gtagttatga tcatgtaccc tccaatatac            3483
Ile Arg Met Arg Phe Leu Asn
                535 tattttacct ggtagattat tgacactttg aaaattggtt gtgtcag gt  gtg caa           3538
                                                   Gly Val Gln
                                                           540 gca act tac tgg gag atg ctt gat gag ggc aga ata tct gaa gtt act           3586
Ala Thr Tyr Trp Glu Met Leu Asp Glu Gly Arg Ile Ser Glu Val Thr
            545                 550                 555 gct aat att ttg atg cag tca gtg gat gag gcg ctt gat cag gtt tct           3634
Ala Asn Ile Leu Met Gln Ser Val Asp Glu Ala Leu Asp Gln Val Ser
                560                 565                 570 aca act tta tgt gat tgg aga ggt cta aaa cca cat gtc aat ttc cca           3682
Thr Thr Leu Cys Asp Trp Arg Gly Leu Lys Pro His Val Asn Phe Pro
            575                 580                 585 aat tac tac aac ttt ctt cat tct aaa gtt gtc cca cgc aag ttg gtc           3730
Asn Tyr Tyr Asn Phe Leu His Ser Lys Val Val Pro Arg Lys Leu Val
                590                 595                 600 aca tac ttt gct gtc gaa aga cta gaa tct gct tgc tac att tct gct           3778
Thr Tyr Phe Ala Val Glu Arg Leu Glu Ser Ala Cys Tyr Ile Ser Ala
605                 610                 615                 620 gcg ttt ctt cgc gca cat aca att gca cga cag caa ttg tat gat ttt           3826
Ala Phe Leu Arg Ala His Thr Ile Ala Arg Gln Gln Leu Tyr Asp Phe
            625                 630                 635 cta g gtatgtacaa tccatactct gcagtctgca tcacactttg aaaacaatga              3880
Leu ctaagaataa aacttgtacc gtatcatcat taattgtcag agttttgtt tgcaagtatc          3940 tcaacttagt aagaacaata cattaaccca accctagttt tgtctcatac ttatctatct         4000
tctctacaca g gg  gag agt aat att ggt tcc att gta atc aat gaa agt          4049
              Gly Glu Ser Asn Ile Gly Ser Ile Val Ile Asn Glu Ser
                            640                 645                 650 gaa aag gaa gga gag gaa gca aaa aag ttc ttg gaa aaa gtc cga tct           4097
Glu Lys Glu Gly Glu Glu Ala Lys Lys Phe Leu Glu Lys Val Arg Ser
                655                 660                 665 tca ttt cct cag gttgagagtc ttgtcatttc tttcgggtga cttatctttc               4149
Ser Phe Pro Gln
            670 ttgcggtgag gcacatataa tctttgatta acattggttt cag gtt ctc cgt gtt           4204
                                                    Val Leu Arg Val gtg aaa aca aaa caa gta aca tat tca gtg ttg aat cat tta ctc ggt           4252
Val Lys Thr Lys Gln Val Thr Tyr Ser Val Leu Asn His Leu Leu Gly
675                 680                 685                 690
```

```
tac att gaa aac ctc gag aag gtt ggc ttg ttg gag gaa aaa gaa atc         4300
Tyr Ile Glu Asn Leu Glu Lys Val Gly Leu Leu Glu Glu Lys Glu Ile
            695                 700                 705 gct cat ctt cat gat gct gtc cag gtaccaaatt aaagaatctc attccttcaa        4354
Ala His Leu His Asp Ala Val Gln
            710 ctatagtctt gtctctttg tcttatgctt ttggtcaaat ctatctctgc ag acc ggc        4412
                                                        Thr Gly
                                                            715 ttg aaa aag ctt ttg aga aac cct cca ata gtt aaa ctt cca aaa ttg         4460
Leu Lys Lys Leu Leu Arg Asn Pro Pro Ile Val Lys Leu Pro Lys Leu
            720                 725                 730 agc gac atg atc acc tca cat ccg tta tcg gtt gct ctt cct cct gca         4508
Ser Asp Met Ile Thr Ser His Pro Leu Ser Val Ala Leu Pro Pro Ala
            735                 740                 745 ttt tgt gaa cct tta aaa cac tcg aaa aaa gaa cca atg aaa ctg cgt         4556
Phe Cys Glu Pro Leu Lys His Ser Lys Lys Glu Pro Met Lys Leu Arg
            750                 755                 760 ggt gtc acg ctt tat aaa gaa ggt tca aag cca act gga gtc tgg ctt         4604
Gly Val Thr Leu Tyr Lys Glu Gly Ser Lys Pro Thr Gly Val Trp Leu
765             770                 775                 780 att ttt gat ggc atc gtt aag gtaacccaaa acttatcttt tacttttaac            4655
Ile Phe Asp Gly Ile Val Lys
                785 tcgtaagtct gtatgatcta ttaccttcat aactgaatgt tataacaatc ctacag tgg       4714
                                                                Trp aaa agt aag atc tta agc aac aat cac tcg ctg cat cca act ttt tct         4762
Lys Ser Lys Ile Leu Ser Asn Asn His Ser Leu His Pro Thr Phe Ser
            790                 795                 800 cac ggt agt aca ttg gga ctc tac gaa gtc ctc act ggg aag cca tat         4810
His Gly Ser Thr Leu Gly Leu Tyr Glu Val Leu Thr Gly Lys Pro Tyr
805             810                 815                 820 ctg tgc gac ttg att aca gat tct atg gtt ctt tgc ttt ttc att gat         4858
Leu Cys Asp Leu Ile Thr Asp Ser Met Val Leu Cys Phe Phe Ile Asp
            825                 830                 835 agc gag aaa att cta tca cta caa tca gat tct acc atc gat gat ttc         4906
Ser Glu Lys Ile Leu Ser Leu Gln Ser Asp Ser Thr Ile Asp Asp Phe
            840                 845                 850 ctt tgg cag gtacgtctct attagaatcc attttagaga gactcatttc                 4955
Leu Trp Gln
        855 ttgattgtta agttgcttca acttttttcg gttttttttg tttgcag gaa agt gca         5011
                                                        Glu Ser Ala ttg gtt ctt ctc aaa ctc ttg cgt cct cag ata ttt gaa agt gtg gca         5059
Leu Val Leu Leu Lys Leu Leu Arg Pro Gln Ile Phe Glu Ser Val Ala
            860                 865                 870 atg caa gaa tta cga gcc ctt gtt tca act gaa agc tcg aaa ctt aca         5107
Met Gln Glu Leu Arg Ala Leu Val Ser Thr Glu Ser Ser Lys Leu Thr
875             880                 885                 890 aca tat gtg acg gga gaa tca atc gaa atc gac tgc aac agc att ggt         5155
Thr Tyr Val Thr Gly Glu Ser Ile Glu Ile Asp Cys Asn Ser Ile Gly
            895                 900                 905 tta tta tta gaa gga ttc gta aaa ccg gtt ggt atc aaa gaa gag ctt         5203
Leu Leu Leu Glu Gly Phe Val Lys Pro Val Gly Ile Lys Glu Glu Leu
            910                 915                 920 ata tca tct ccc gcc gca tta tca cct tct aac ggg aat caa agc ttc         5251
Ile Ser Ser Pro Ala Ala Leu Ser Pro Ser Asn Gly Asn Gln Ser Phe
            925                 930                 935
```

```
cat aat tca tca gaa gct tca g gtaattaatt gcacagtaca gcaggatcaa         5303
His Asn Ser Ser Glu Ala Ser
    940             945 acctttttaa atgtcagcga atgatataaa tcgaattaaa tcaaaaatgt gttttgtttt       5363
tttgaccaca g gt atc atg aga gtc agt ttc tca caa caa gca aca cag        5412
            Gly Ile Met Arg Val Ser Phe Ser Gln Gln Ala Thr Gln
                                950                 955 tat att gtt gag acg aga gca aga gca atc atc ttc aac att gga gca        5460
Tyr Ile Val Glu Thr Arg Ala Arg Ala Ile Ile Phe Asn Ile Gly Ala
    960             965                 970 ttt gga gct gat agg act cta cat cga aga cca tct tcg tta aca cca        5508
Phe Gly Ala Asp Arg Thr Leu His Arg Arg Pro Ser Ser Leu Thr Pro
975             980                 985                 990 cca cgt agc tca agc tct gat cag ctt cag aga tca ttt cgt aaa gaa        5556
Pro Arg Ser Ser Ser Ser Asp Gln Leu Gln Arg Ser Phe Arg Lys Glu
                995                 1000                1005 cac aga ggt ctc atg agc tgg cct gaa aat att tac gcc aaa caa           5601
His Arg Gly Leu Met Ser Trp Pro Glu Asn Ile Tyr Ala Lys Gln
            1010                1015                1020 caa caa gag atc aat aaa acg aca tta agt tta tct gaa cga gca           5646
Gln Gln Glu Ile Asn Lys Thr Thr Leu Ser Leu Ser Glu Arg Ala
            1025                1030                1035 atg caa ctc agc att ttc ggc agc atg gtaaaaaaga tctcaatgtt              5693
Met Gln Leu Ser Ile Phe Gly Ser Met
            1040            1045 gattctttta aaggttgtta tcgatgaact tctcgactaa cctgaaggtt tttatcttct      5753
gatattctcg aatatag gtt aat gtg tac aga agg agt gta agt ttc ggt         5803
                   Val Asn Val Tyr Arg Arg Ser Val Ser Phe Gly
                                    1050                1055 ggg atc tat aat aac aag tta caa gat aac ttg ttg tac aaa aaa           5848
Gly Ile Tyr Asn Asn Lys Leu Gln Asp Asn Leu Leu Tyr Lys Lys
        1060                1065                1070 ctt cca cta aac cca gct caa ggt ctc gtt tca gcc aaa tca gaa           5893
Leu Pro Leu Asn Pro Ala Gln Gly Leu Val Ser Ala Lys Ser Glu
        1075                1080                1085 agt tca att gtg acc aag aag cag ctt gaa acc cgt aaa cat gcg           5938
Ser Ser Ile Val Thr Lys Lys Gln Leu Glu Thr Arg Lys His Ala
        1090                1095                1100 tgt cag ctt cct ctg aaa ggg gaa agc agc aca agg caa aat acg           5983
Cys Gln Leu Pro Leu Lys Gly Glu Ser Ser Thr Arg Gln Asn Thr
        1105                1110                1115 atg gtt gaa tca agc gat gaa gaa gat gaa gat gaa gga atc gtt           6028
Met Val Glu Ser Ser Asp Glu Glu Asp Glu Asp Glu Gly Ile Val
        1120                1125                1130 gtg aga atc gat tct ccg agt aaa atc gtt ttc agg aac gat cta           6073
Val Arg Ile Asp Ser Pro Ser Lys Ile Val Phe Arg Asn Asp Leu
        1135                1140                1145 tga                                                                    6076

<210> SEQ ID NO 2
<211> LENGTH: 1146
<212> TYPE: PRT
<213> ORGANISM: Arabidopsis thaliana

<400> SEQUENCE: 2

Met Thr Thr Val Ile Asp Ala Thr Met Ala Tyr Arg Phe Leu Glu Glu
1               5                   10                  15

Ala Thr Asp Ser Ser Ser Ser Ser Ser Ser Lys Leu Glu Ser Ser
            20                  25                  30
```

-continued

Pro Val Asp Ala Val Leu Phe Val Gly Met Ser Leu Val Leu Gly Ile
         35                  40                  45

Ala Ser Arg His Leu Leu Arg Gly Thr Arg Val Pro Tyr Thr Val Ala
 50                      55                  60

Leu Leu Val Ile Gly Ile Ala Leu Gly Ser Leu Glu Tyr Gly Ala Lys
 65                  70                  75                  80

His Asn Leu Gly Lys Ile Gly His Gly Ile Arg Ile Trp Asn Glu Ile
                 85                      90                  95

Asp Pro Glu Leu Leu Leu Ala Val Phe Leu Pro Ala Leu Leu Phe Glu
                100                 105                 110

Ser Ser Phe Ser Met Glu Val His Gln Ile Lys Arg Cys Leu Gly Gln
                115                 120                 125

Met Val Leu Leu Ala Val Pro Gly Val Leu Ile Ser Thr Ala Cys Leu
        130                 135                 140

Gly Ser Leu Val Lys Val Thr Phe Pro Tyr Glu Trp Asp Trp Lys Thr
145                 150                 155                 160

Ser Leu Leu Leu Gly Gly Leu Leu Ser Ala Thr Asp Pro Val Ala Val
                165                 170                 175

Val Ala Leu Leu Lys Glu Leu Gly Ala Ser Lys Lys Leu Ser Thr Ile
                180                 185                 190

Ile Glu Gly Glu Ser Leu Met Asn Asp Gly Thr Ala Ile Val Val Phe
        195                 200                 205

Gln Leu Phe Leu Lys Met Ala Met Gly Gln Asn Ser Asp Trp Ser Ser
        210                 215                 220

Ile Ile Lys Phe Leu Leu Lys Val Ala Leu Gly Ala Val Gly Ile Gly
225                 230                 235                 240

Leu Ala Phe Gly Ile Ala Ser Val Ile Trp Leu Lys Phe Ile Phe Asn
                245                 250                 255

Asp Thr Val Ile Glu Ile Thr Leu Thr Ile Ala Val Ser Tyr Phe Ala
                260                 265                 270

Tyr Tyr Thr Ala Gln Glu Trp Ala Gly Ala Ser Gly Val Leu Thr Val
        275                 280                 285

Met Thr Leu Gly Met Phe Tyr Ala Ala Phe Ala Arg Thr Ala Phe Lys
        290                 295                 300

Gly Asp Ser Gln Lys Ser Leu His His Phe Trp Glu Met Val Ala Tyr
305                 310                 315                 320

Ile Ala Asn Thr Leu Ile Phe Ile Leu Ser Gly Val Val Ile Ala Glu
                325                 330                 335

Gly Ile Leu Asp Ser Asp Lys Ile Ala Tyr Gln Gly Asn Ser Trp Arg
                340                 345                 350

Phe Leu Phe Leu Leu Tyr Val Tyr Ile Gln Leu Ser Arg Val Val Val
        355                 360                 365

Val Gly Val Leu Tyr Pro Leu Leu Cys Arg Phe Gly Tyr Gly Leu Asp
        370                 375                 380

Trp Lys Glu Ser Ile Ile Leu Val Trp Ser Gly Leu Arg Gly Ala Val
385                 390                 395                 400

Ala Leu Ala Leu Ser Leu Ser Val Lys Gln Ser Ser Gly Asn Ser His
                405                 410                 415

Ile Ser Lys Glu Thr Gly Thr Leu Phe Leu Phe Phe Thr Gly Gly Ile
                420                 425                 430

Val Phe Leu Thr Leu Ile Val Asn Gly Ser Thr Thr Gln Phe Val Leu
        435                 440                 445

```
Arg Leu Leu Arg Met Asp Ile Leu Pro Ala Pro Lys Lys Arg Ile Leu
    450                 455                 460
Glu Tyr Thr Lys Tyr Glu Met Leu Asn Lys Ala Leu Arg Ala Phe Gln
465                 470                 475                 480
Asp Leu Gly Asp Glu Glu Leu Gly Pro Ala Asp Trp Pro Thr Val
                485                 490                 495
Glu Ser Tyr Ile Ser Ser Leu Lys Gly Ser Glu Gly Glu Leu Val His
                500                 505                 510
His Pro His Asn Gly Ser Lys Ile Gly Ser Leu Asp Pro Lys Ser Leu
            515                 520                 525
Lys Asp Ile Arg Met Arg Phe Leu Asn Gly Val Gln Ala Thr Tyr Trp
        530                 535                 540
Glu Met Leu Asp Glu Gly Arg Ile Ser Glu Val Thr Ala Asn Ile Leu
545                 550                 555                 560
Met Gln Ser Val Asp Glu Ala Leu Asp Gln Val Ser Thr Thr Leu Cys
                565                 570                 575
Asp Trp Arg Gly Leu Lys Pro His Val Asn Phe Pro Asn Tyr Tyr Asn
                580                 585                 590
Phe Leu His Ser Lys Val Val Pro Arg Lys Leu Val Thr Tyr Phe Ala
            595                 600                 605
Val Glu Arg Leu Glu Ser Ala Cys Tyr Ile Ser Ala Ala Phe Leu Arg
        610                 615                 620
Ala His Thr Ile Ala Arg Gln Gln Leu Tyr Asp Phe Leu Gly Glu Ser
625                 630                 635                 640
Asn Ile Gly Ser Ile Val Ile Asn Glu Ser Glu Lys Glu Gly Glu Glu
                645                 650                 655
Ala Lys Lys Phe Leu Glu Lys Val Arg Ser Ser Phe Pro Gln Val Leu
            660                 665                 670
Arg Val Val Lys Thr Lys Gln Val Thr Tyr Ser Val Leu Asn His Leu
        675                 680                 685
Leu Gly Tyr Ile Glu Asn Leu Glu Lys Val Gly Leu Leu Glu Glu Lys
    690                 695                 700
Glu Ile Ala His Leu His Asp Ala Val Gln Thr Gly Leu Lys Lys Leu
705                 710                 715                 720
Leu Arg Asn Pro Pro Ile Val Lys Leu Pro Lys Leu Ser Asp Met Ile
                725                 730                 735
Thr Ser His Pro Leu Ser Val Ala Leu Pro Ala Phe Cys Glu Pro
                740                 745                 750
Leu Lys His Ser Lys Lys Glu Pro Met Lys Leu Arg Gly Val Thr Leu
            755                 760                 765
Tyr Lys Glu Gly Ser Lys Pro Thr Gly Val Trp Leu Ile Phe Asp Gly
        770                 775                 780
Ile Val Lys Trp Lys Ser Lys Ile Leu Ser Asn Asn His Ser Leu His
785                 790                 795                 800
Pro Thr Phe Ser His Gly Ser Thr Leu Gly Leu Tyr Glu Val Leu Thr
                805                 810                 815
Gly Lys Pro Tyr Leu Cys Asp Leu Ile Thr Asp Ser Met Val Leu Cys
            820                 825                 830
Phe Phe Ile Asp Ser Glu Lys Ile Leu Ser Leu Gln Ser Asp Ser Thr
        835                 840                 845
Ile Asp Asp Phe Leu Trp Gln Glu Ser Ala Leu Val Leu Leu Lys Leu
    850                 855                 860
Leu Arg Pro Gln Ile Phe Glu Ser Val Ala Met Gln Glu Leu Arg Ala
```

```
                865                 870                 875                 880
Leu Val Ser Thr Glu Ser Ser Lys Leu Thr Thr Tyr Val Thr Gly Glu
                    885                 890                 895

Ser Ile Glu Ile Asp Cys Asn Ser Ile Gly Leu Leu Glu Gly Phe
                900                 905                 910

Val Lys Pro Val Gly Ile Lys Glu Glu Leu Ile Ser Ser Pro Ala Ala
            915                 920                 925

Leu Ser Pro Ser Asn Gly Asn Gln Ser Phe His Asn Ser Ser Glu Ala
        930                 935                 940

Ser Gly Ile Met Arg Val Ser Phe Ser Gln Gln Ala Thr Gln Tyr Ile
945                 950                 955                 960

Val Glu Thr Arg Ala Arg Ala Ile Ile Phe Asn Ile Gly Ala Phe Gly
                965                 970                 975

Ala Asp Arg Thr Leu His Arg Arg Pro Ser Ser Leu Thr Pro Pro Arg
                980                 985                 990

Ser Ser Ser Ser Asp Gln Leu Gln  Arg Ser Phe Arg Lys  Glu His Arg
                995                 1000                1005

Gly Leu Met Ser Trp Pro Glu  Asn Ile Tyr Ala Lys  Gln Gln Gln
    1010                1015                1020

Glu Ile Asn Lys Thr Thr Leu  Ser Leu Ser Glu Arg  Ala Met Gln
    1025                1030                1035

Leu Ser Ile Phe Gly Ser Met  Val Asn Val Tyr Arg  Arg Ser Val
    1040                1045                1050

Ser Phe Gly Gly Ile Tyr Asn  Asn Lys Leu Gln Asp  Asn Leu Leu
    1055                1060                1065

Tyr Lys Lys Leu Pro Leu Asn  Pro Ala Gln Gly Leu  Val Ser Ala
    1070                1075                1080

Lys Ser Glu Ser Ser Ile Val  Thr Lys Lys Gln Leu  Glu Thr Arg
    1085                1090                1095

Lys His Ala Cys Gln Leu Pro  Leu Lys Gly Glu Ser  Ser Thr Arg
    1100                1105                1110

Gln Asn Thr Met Val Glu Ser  Asp Glu Glu Asp  Glu Asp Glu
    1115                1120                1125

Gly Ile Val Val Arg Ile Asp  Ser Pro Ser Lys Ile  Val Phe Arg
    1130                1135                1140

Asn Asp Leu
    1145

<210> SEQ ID NO 3
<211> LENGTH: 822
<212> TYPE: PRT
<213> ORGANISM: Cricetulus griseus

<400> SEQUENCE: 3

Met Met Leu Arg Trp Ser Gly Ile Trp Gly Leu Ser Pro Pro Arg Ile
1               5                   10                  15

Phe Pro Ser Leu Leu Val Val Val Ala Leu Val Gly Leu Leu Pro Val
                20                  25                  30

Leu Arg Ser His Gly Leu Gln Pro Ser Pro Thr Ala Asn Thr Ile Arg
            35                  40                  45

Gly Ala Glu Pro Pro Arg Glu Arg Ser Ile Gly Asp Val Thr Thr Ala
        50                  55                  60

Pro Ser Glu Pro Val His His Pro Asp Asp Arg Asn Leu Thr Asn Leu
65                  70                  75                  80
```

-continued

```
His Ile Glu His Gly Ala Lys Thr Leu Arg Lys Ala Phe Pro Val Leu
                 85                  90                  95

Asp Ile Asp Tyr Leu His Val Arg Thr Pro Phe Glu Ile Ser Leu Trp
            100                 105                 110

Ile Leu Leu Ala Cys Leu Met Lys Ile Gly Phe His Val Ile Pro Thr
                115                 120                 125

Ile Ser Ser Ile Val Pro Glu Ser Cys Leu Ile Val Val Gly Leu
130                 135                 140

Leu Val Gly Gly Leu Ile Lys Gly Val Gly Glu Thr Pro Pro Phe Leu
145                 150                 155                 160

Gln Ser Asp Val Phe Phe Leu Phe Leu Pro Pro Ile Ile Leu Asp
                165                 170                 175

Ala Gly Tyr Phe Leu Pro Leu Arg Gln Phe Thr Glu Asn Leu Gly Thr
            180                 185                 190

Ile Leu Ile Phe Ala Val Val Gly Thr Leu Trp Asn Ala Phe Phe Leu
            195                 200                 205

Gly Gly Leu Leu Tyr Ala Val Cys Leu Val Gly Gly Glu Gln Ile Asn
            210                 215                 220

Asn Ile Gly Leu Leu Asp Thr Leu Leu Phe Gly Ser Ile Ile Ser Ala
225                 230                 235                 240

Val Asp Pro Val Ala Val Val Ala Val Phe Glu Glu Ile His Ile Asn
                245                 250                 255

Glu Leu Leu His Ile Leu Val Phe Gly Glu Ser Leu Leu Asn Asp Ala
            260                 265                 270

Val Thr Val Val Leu Tyr His Leu Phe Glu Glu Phe Ala Asn Tyr Asp
            275                 280                 285

Ser Ile Gly Ile Ser Asp Ile Phe Leu Gly Phe Leu Ser Phe Phe Val
            290                 295                 300

Val Ala Leu Gly Gly Val Phe Val Gly Val Val Tyr Gly Val Ile Ala
305                 310                 315                 320

Ala Phe Thr Ser Arg Phe Thr Ser His Ile Arg Val Ile Glu Pro Leu
                325                 330                 335

Phe Val Phe Leu Tyr Ser Tyr Met Ala Tyr Leu Ser Ala Glu Leu Phe
            340                 345                 350

His Leu Ser Gly Ile Met Ala Leu Ile Ala Ser Gly Val Val Met Arg
            355                 360                 365

Pro Tyr Val Glu Ala Asn Ile Ser His Lys Ser His Thr Thr Ile Lys
370                 375                 380

Tyr Phe Leu Lys Met Trp Ser Ser Val Ser Glu Thr Leu Ile Phe Ile
385                 390                 395                 400

Phe Leu Gly Val Ser Thr Val Ala Gly Ser His Gln Trp Asn Trp Thr
                405                 410                 415

Phe Val Ile Ser Thr Leu Leu Phe Cys Leu Ile Ala Arg Val Leu Gly
            420                 425                 430

Val Leu Val Leu Thr Trp Phe Ile Asn Lys Phe Arg Ile Val Lys Leu
            435                 440                 445

Thr Pro Lys Asp Gln Phe Ile Ile Ala Tyr Gly Gly Leu Arg Gly Ala
450                 455                 460

Ile Ala Phe Ser Leu Gly Tyr Leu Met Asp Lys Lys His Phe Pro Met
465                 470                 475                 480

Cys Asp Leu Phe Leu Thr Ala Ile Ile Thr Val Ile Phe Phe Thr Val
                485                 490                 495

Phe Val Gln Gly Met Thr Ile Arg Pro Leu Val Asp Leu Leu Ala Val
```

-continued

```
                    500                 505                 510
Lys Lys Lys Gln Glu Thr Lys Arg Ser Ile Asn Glu Glu Ile His Thr
            515                 520                 525

Gln Phe Leu Asp His Leu Leu Thr Gly Ile Glu Asp Ile Cys Gly His
        530                 535                 540

Tyr Gly His His His Trp Lys Asp Lys Leu Asn Arg Phe Asn Lys Lys
545                 550                 555                 560

Tyr Val Lys Lys Cys Leu Ile Ala Gly Glu Arg Ser Lys Glu Pro Gln
                565                 570                 575

Leu Ile Ala Phe Tyr His Lys Met Glu Met Lys Gln Ala Ile Glu Leu
        580                 585                 590

Val Glu Ser Gly Gly Met Gly Lys Ile Pro Ser Ala Val Ser Thr Val
            595                 600                 605

Ser Met Gln Asn Ile His Pro Lys Ser Met Ala Ser Glu Arg Ile Leu
        610                 615                 620

Pro Ala Leu Ser Lys Asp Lys Glu Glu Ile Arg Lys Ile Leu Arg
625                 630                 635                 640

Ser Asn Leu Gln Lys Thr Arg Gln Arg Leu Arg Ser Tyr Asn Arg His
                645                 650                 655

Thr Leu Val Ala Asp Pro Tyr Glu Glu Ala Trp Asn Gln Met Leu Leu
            660                 665                 670

Arg Arg Gln Lys Ala Arg Gln Leu Glu Gln Lys Met Ser Asn Tyr Leu
        675                 680                 685

Thr Val Pro Ala His Lys Leu Asp Ser Pro Thr Met Ser Arg Ala Arg
        690                 695                 700

Ile Gly Ser Asp Pro Leu Ala Tyr Glu Pro Lys Ala Asp Leu Pro Val
705                 710                 715                 720

Ile Thr Ile Asp Pro Ala Ser Pro Gln Ser Pro Glu Ser Val Asp Leu
                725                 730                 735

Val Asn Glu Glu Leu Lys Ala Lys Val Leu Gly Val Asn Arg Asp Pro
            740                 745                 750

Thr Arg Leu Thr Arg Gly Glu Glu Asp Glu Asp Glu Asp Gly
        755                 760                 765

Val Ile Met Met Arg Arg Lys Glu Pro Ser Ser Pro Gly Thr Asp Val
        770                 775                 780

Phe Thr Pro Ala Pro Met Tyr Ser Pro Ser Ser Gln Arg Ile Gln Arg
785                 790                 795                 800

Cys Leu Ser Asp Pro Gly Pro His Pro Glu Pro Gly Glu Gly Glu Pro
                805                 810                 815

Phe Ile Pro Lys Gly Glu
            820
```

<210> SEQ ID NO 4
<211> LENGTH: 424
<212> TYPE: PRT
<213> ORGANISM: Pseudomonas aeruginosa

<400> SEQUENCE: 4

```
Met Leu Asp Leu Val Ala Ala Phe Ile Ala Leu Thr Thr Leu Leu Thr
1               5                   10                  15

Tyr Val Asn Tyr Arg Phe Ile Arg Leu Pro Pro Thr Ile Gly Val Met
            20                  25                  30

Ala Thr Ala Leu Val Phe Ser Leu Ile Val Gln Gly Leu Ser Glu Leu
        35                  40                  45
```

-continued

```
Gly Tyr Pro Ile Leu Glu Val Glu Met Gln Glu Ile Ile Arg Arg Ile
 50                  55                  60

Asp Phe Ser Glu Val Leu Met Thr Trp Phe Leu Pro Ala Leu Leu Phe
 65                  70                  75                  80

Ala Gly Ala Leu His Val Asp Leu Ser Asp Leu Arg Ser Tyr Lys Trp
                 85                  90                  95

Pro Ile Gly Leu Leu Ala Thr Ala Gly Val Leu Ile Ala Thr Phe Val
            100                 105                 110

Ile Gly Gly Leu Ala Tyr Tyr Thr Phe Pro Leu Phe Gly Trp Gln Val
        115                 120                 125

Asp Phe Ile Tyr Cys Leu Leu Phe Gly Ala Leu Ile Ser Pro Thr Asp
130                 135                 140

Pro Ile Ala Val Leu Gly Ile Leu Lys Ser Ala Gly Ala Pro Lys Pro
145                 150                 155                 160

Leu Ala Thr Thr Ile Val Gly Glu Ser Leu Phe Asn Asp Gly Thr Ala
                165                 170                 175

Val Val Val Phe Ala Ile Ile Leu Gly Ile Leu Gln Leu Gly Glu Ala
            180                 185                 190

Pro Thr Val Ser Ala Thr Ala Ile Leu Phe Val Gln Glu Ala Ile Gly
        195                 200                 205

Gly Val Val Phe Gly Ala Val Leu Gly Tyr Gly Val Phe Val Met Met
210                 215                 220

Arg Gly Ile Asp Gln Tyr Gln Val Glu Val Met Leu Thr Leu Ala Leu
225                 230                 235                 240

Val Ile Gly Gly Ala Ala Leu Ala Ala Arg Leu His Val Ser Ala Pro
                245                 250                 255

Ile Ala Met Val Val Ala Gly Leu Ile Ile Gly Asn His Gly Arg His
            260                 265                 270

Tyr Ala Met Ser Asp Glu Thr Arg Arg Tyr Val Asp Lys Phe Trp Glu
        275                 280                 285

Leu Ile Asp Glu Ile Leu Asn Ala Leu Leu Phe Ala Leu Ile Gly Leu
290                 295                 300

Glu Leu Leu Leu Leu Pro Phe Ser Trp Leu His Val Ala Ala Ala Phe
305                 310                 315                 320

Ala Leu Gly Gly Ala Val Leu Val Ser Arg Leu Leu Thr Val Gly Pro
                325                 330                 335

Ala Ile Leu Val Leu Arg Arg Phe Arg Gly Ala Asn Arg Gln Val Pro
            340                 345                 350

Ala Gly Thr Ile Arg Ile Leu Val Trp Gly Gly Leu Arg Gly Gly Val
        355                 360                 365

Ser Val Ala Leu Ala Leu Ser Leu Pro Leu Gly Pro Glu Arg Asp Leu
370                 375                 380

Ile Leu Ser Leu Thr Tyr Ile Val Val Leu Val Ser Ile Leu Leu Gln
385                 390                 395                 400

Gly Leu Ser Ile Gly Pro Leu Val Arg Arg Ile Tyr Ala Gly Gln Pro
                405                 410                 415

Leu Glu Lys Ser Glu Gly Ala His
            420
```

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

```
<400> SEQUENCE: 5
ggatgatgat cgattcggat                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6
atctgactca taggatatcg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
ccttcacatc caaaacccac                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
gcacataccc acaaccagaa                                               20

<210> SEQ ID NO 9
<211> LENGTH: 23
<212> TYPE: DNA
<213> ORGANISM: Artificial Sequence
<220> FEATURE:
<223> OTHER INFORMATION: Synthetic DNA

<400> SEQUENCE: 9
gaatgttttg aaggatatct cag                                           23

<210> SEQ ID NO 10
<211> LENGTH: 21
<212> TYPE: DNA
<213> ORGANISM: Artificial Sequence
<220> FEATURE:
<223> OTHER INFORMATION: Synthetic DNA

<400> SEQUENCE: 10
gaaaaatgga gcacgaaatg c                                             21

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11
cccgagatta atacacaatc                                               20

<210> SEQ ID NO 12
```

-continued

```
<211> LENGTH: 21
<212> TYPE: DNA
<213> ORGANISM: Artificial Sequence
<220> FEATURE:
<223> OTHER INFORMATION: Synthetic DNA

<400> SEQUENCE: 12
gcagattatg taattgtgac c                                           21

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
tcgtgtttac cgggtcggat                                             20

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA

<400> SEQUENCE: 14
tgatgagaat cttagcgagc                                             20

<210> SEQ ID NO 15
<211> LENGTH: 21
<212> TYPE: DNA
<213> ORGANISM: Artificial Sequence
<220> FEATURE:
<223> OTHER INFORMATION: Synthetic DNA

<400> SEQUENCE: 15
tggtaagacc aaattacact c                                           21

<210> SEQ ID NO 16
<211> LENGTH: 23
<212> TYPE: DNA
<213> ORGANISM: Artificial Sequence
<220> FEATURE:
<223> OTHER INFORMATION: Synthetic DNA

<400> SEQUENCE: 16
cgtaattaaa atgtgttaaa ccg                                         23

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
aaccgcatag tacaatgcag                                             20

<210> SEQ ID NO 18
<211> LENGTH: 22
<212> TYPE: DNA
<213> ORGANISM: Artificial Sequence
<220> FEATURE:
<223> OTHER INFORMATION: Synthetic DNA

<400> SEQUENCE: 18
```

```
cggtaaagat caactaataa cg                                              22

<210> SEQ ID NO 19
<211> LENGTH: 20
<212> TYPE: DNA
<213> ORGANISM: Artificial Sequence
<220> FEATURE:
<223> OTHER INFORMATION: Synthetic DNA

<400> SEQUENCE: 19
aacggaaacg gcaactagac                                                 20

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA

<400> SEQUENCE: 20
accctaaatg tttcgattcg                                                 20
```

PROTEINS AND DNA RELATED TO SALT TOLERANCE IN PLANTS

CROSS-REFERENCE TO RELATED APPLICATIONS

This application claims benefit to U.S. provisional application No. 60/194,648, filed on Apr. 4, 2000, and incorporated herein by reference in its entirety.

STATEMENT OF FEDERALLY FUNDED RESEARCH

This invention was supported by the National Institutes of Health by Contract No. R01GM59138. The government may have certain rights to this invention.

BACKGROUND OF THE INVENTION

1. Field of the Invention

The present invention relates to proteins and nucleic acids related to salt tolerance in plants.

2. Description of the Background

Soil salinity is a major abiotic stress for plant agriculture. Sodium ions in saline soils are toxic to plants due to its adverse effects on $K^+$ nutrition, cytosolic enzyme activities, photosynthesis and metabolism (1, 2). Three mechanisms function cooperatively to prevent the accumulation of $Na^+$ in the cytoplasm, i.e. restriction of $Na^+$ influx, active $Na^+$ efflux and compartmentation of $Na^+$ in the vacuole (1). The wheat high-affinity $K^+$ transporter HKT1 functions as a $Na^+$-$K^+$ cotransporter, which confers low-affinity $Na^+$ uptake at toxic $Na^+$ concentrations (3). Thus HKT1 could represent one of the $Na^+$ uptake pathways in plant roots. The low-affinity cation transporter LCT1 from wheat may also mediate $Na^+$ influx into plant cells (4). In addition, patch clamp studies have shown that non-selective cation channels play important roles in mediating $Na^+$ entry into plants (5). The *Arabidopsis thaliana* AtNHX1 gene encodes a tonoplast $Na^+/H^+$ antiporter and functions in compartmentalizing $Na^+$ into the vacuole (6). Over-expression of AtNHX1 enhances the salt tolerance of *Arabidopsis* plants (7).

No $Na^+$ efflux transporter has been cloned from plants. Plants do not appear to have a $Na^+$-ATPase at the plasma membrane (1). It is expected that proton motive force created by $H^+$-ATPases would drive $Na^+$ efflux from plant cells through plasma membrane $Na^+$/H+antiporters (8). Fungal cells contain both $Na^+$-ATPases and $Na^+/H^+$ antiporters at the plasma membrane. In the yeast *Saccharomyces cerevisiae*, plasma membrane $Na^{+}$-ATPases play a predominant role in $Na^+$ efflux and salt tolerance (9). In contrast, $Na^+/H^+$ antiporters are more important for $Na^+$ efflux and salt tolerance in the fungus *Schizosaccharomyces pombe* (10).

Recently, several *Arabidopsis* sos (for salt overly sensitive) mutants defective in salt tolerance were characterized (11, 12, 13). The sos mutants are specifically hypersensitive to high external $Na^+$ or $Li^+$ and also unable to grow under very low external $K^+$ concentrations (13). Allelic tests indicated that the sos mutants define three SOS loci, i.e., SOS1, SOS2 and SOS3 (13). The SOS3 gene encodes an EF-hand type calcium-binding protein with similarities to animal neuronal calcium sensors and the yeast calcineurin B subunit (14). In yeast, calcineurin plays a central role in the regulation of $Na^+$ and $K^+$ transport. Mutations in calcineurin B lead to increased sensitivity of yeast cells to growth inhibition by $Na^+$ and $Li^+$ stresses (15). The SOS2 gene was recently cloned and shown to encode a serine/threonine type protein kinase (16). Interestingly, SOS2 physically interacts with and is activated by SOS3 (17). Therefore, SOS2 and SOS3 define a novel regulatory pathway for $Na^+$ and $K^+$ homeostasis and salt tolerance in plants. The SOS3/SOS2 pathway has been predicted to control the expression and/or activity of ion transporters (17). However, the identities of the transporters regulated by this pathway are not known.

Among the three SOS loci, SOS1 plays the greatest role in plant salt tolerance. Compared to sos2 and sos3 mutant plants, sos1 mutant plants are even more sensitive to $Na^+$ and $Li^+$ stresses (13). Double mutant analysis indicated that SOS1 functions in the same pathway as SOS2 and SOS3 (12, 13). Thus, SOS1 may be a target for regulation by the SOS3/SOS2 pathway.

Accordingly, there remains a need in the art to isolate the SOS1 gene and the protein encoded thereby.

Furthermore, because of limited water supplies and the widespread use of irrigation, the soils of many cultivated areas have become increasingly salinized. In particular, modern agricultural practices such as irrigation impart increasing salt concentrations when the available irrigation water evaporates and leaves previously dissolved salts behind. As a result, the development of salt tolerant cultivars of agronomically important crops has become important in many parts of the world. For example, in salty soil found in areas such as Southern California, Arizona, New Mexico and Texas.

Dissolved salts in the soil increase the osmotic pressure of the solution in the soil and tend to decrease the rate at which water from the soil will enter the roots. If the solution in the soil becomes too saturated with dissolved salts, the water may actually be withdrawn from the plant roots. Thus the plants slowly starve though the supply of water and dissolved nutrients may be more than ample. Also, elements such as sodium are known to be toxic to plants when they are taken up by the plants.

Salt tolerant plants can facilitate use of marginal areas for crop production, or allow a wider range of sources of irrigation water. Traditional plant breeding methods have, thus far, not yielded substantial improvements in salt tolerance and growth of crop plants. In addition, such methods require long term selection and testing before new cultivars can be identified.

Accordingly, there is a need to increase salt tolerance in plants, particularly those plants which are advantageously useful as agricultural crops.

SUMMARY OF THE INVENTION

The present invention is based, in part, on the isolation of the SOS1 locus through positional cloning. It is predicted to encode a transmembrane protein with similarities to plasma membrane $Na^+/H^+$ antiporters from bacteria and fungi. The results of the present invention suggest that a plasma membrane-type $Na^+/H^+$ antiporter is essential for plant salt tolerance. The steady state level of SOS1 transcript is up-regulated by NaCl stress. The sos2 mutation abolishes SOS1 up-regulation in the shoot. In the sos3 mutant, no SOS1 up-regulation is found in the shoot or root. Therefore, SOS1 gene expression under NaCl stress is controlled by the SOS3/SOS2 regulatory pathway.

Accordingly, the present invention provides an isolated polynucleotide which encodes a protein comprising the amino acid sequence of SEQ ID NO:2.

In a preferred embodiment the polypeptide has Na+/H+ transporter activity.

In another preferred embodiment the polynucleotide comprises SEQ ID NO:1, polynucleotides which are complimentary to SEQ ID NO:1, polynucleotides which are at least 70%, 80% and 90% identical to SEQ ID NO:1; or those sequence which hybridize under stringent conditions to SEQ ID NO:1, the stringent conditions comprise washing in 5×SSC at a temperature from 50 to 68° C.

In another preferred embodiment the polynucleotides of the present invention are in a vector and/or a host cell. Preferably, the polynucleotides are in a plant cell or transgenic plant. Preferably, the plant is *Arabidopsis thaliania* or selected from the group consisting of wheat, corn, peanut cotton, oat, and soybean plant. In a preferred embodiment, the polynucleotides are operably linked to a promoter, preferably an inducible promoter.

In another preferred embodiment the present invention provides, a process for screening for polynucleotides which encode a protein having Na+/K+ transporter activity comprising hybridizing the polynucleotide of the invention to the polynucleotide to be screened; expressing the polynucleotide to produce a protein; and detecting the presence or absence of Na+/K+ transporter activity in said protein.

In another preferred embodiment, the present invention provides a method for detecting a nucleic acid with at least 70% homology to nucleotide SEQ ID NO:1, sequences which are complimentary to SEQ ID NO:1 and/or which encode a protein having the amino acid sequence in SEQ ID NO:2 comprising contacting a nucleic acid sample with a probe or primer comprising at least 15 consecutive nucleotides of the nucleotide sequence of claim 1, or at least 15 consecutive nucleotides of the complement thereof.

In another preferred embodiment, the present invention provides a method for producing a nucleic acid with at least 70% homology to the polynucleotides of the present invention comprising contacting a nucleic acid sample with a primer comprising at least 15 consecutive nucleotides of the nucleotide sequence of claim 3, or at least 15 consecutive nucleotides of the complement thereof.

In another preferred embodiment, the present invention provides a method for making SOS2 protein, comprising culturing the host cell carrying the polynucleotides of the invention for a time and under conditions suitable for expression of SOS2, and collecting the SOS2 protein.

In another preferred embodiment, the present invention provides a method of making a transgenic plant comprising introducing the polynucleotides of the invention into the plant.

In another preferred embodiment, the present invention provides method of increasing the salt tolerance of a plant in need thereof, comprising introducing the polynucleotides of the invention into said plant.

In another preferred embodiment, the present invention provides an isolated polypeptide comprising the amino acid sequence in SEQ ID NO:2 or those proteins that are at least 70%, preferably 80%, preferably 90% and preferably 95% identity to SEQ ID NO:2. Preferably, the polypeptides have Na+/K+ transporter activity.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 3. SOS1 is predicted to encode a transmembrane protein. (A) The deduced amino acid sequence of SOS1 (SEQ ID NO:2). The 12 putative transmembrane domains (TM) are underlined. (B) Hydrophobicity plot of SOS1. The hydrophobicity values were calculated by the program Tmpred available at publicly available sources.

FIG. 4. SOS1, is similar to $Na^+/H^+$ antiporters. (A) Alignment of SOS1 SEQ ID NO:2 (accession number AF256224) with $Na^+/H^+$ antiporters NHE1 from Chinese hamster SEQ ID NO:3 (P48761) and NhaP from *Pseudomonas aeruginosa* SEQ ID NO:4 (BAA31695). The sequences were aligned by the program ClustalW. Amino acids identical in at least two proteins are highlighted in black and conservative substitutions in grey. * indicates conserved residues that were substituted in sos1 mutant alleles. (B) Phylogenetic analysis of SOS1 and other representative $Na^+/H^+$ antiporters. Multiple sequence alignment was performed with ClustalW. The alignment is based on the N-terminal 450 amino acids of SOS1. Evolutionary distances were calculated by the Neighbor Joining method and the phylogenetic tree was drawn by the program Drawgram. The accession number and source of each of the other representative $Na^+/H^+$ antiporters are as follows: NHE1 (P19634), *Homo sapiens*; NHE2 (AAD41635), *Homo sapiens*; NHE3 (P48764), *Homo sapiens*; NHE4 (P26434), *Rattus norvegicus*; NIBS (AAC98696.1), *Homo sapiens*; NHE6 (NP 006350), *Homo sapiens*; NHA1 (NP_013239), *Saccharomyces cerevisiae*; NHX1 (NP 010744), *Saccharomyces cerevisiae*; AtNHX1 (AAD 16946.1), *Arabidopsis thaliana*; SOD2 (CAA77796.1), *Schizosaccharomyces pombe*; NhaA (P13738), *Escherichia coli*; NhaP (BAA31695.1), *Pseudomonas aeruginosa*.

FIG. 6. SOS1 expression is up-regulated by NaCl stress and is under control of the SOS3/SOS2 regulatory pathway. (A) SOS1 expression is specifically up-regulated by NaCl stress in wild type *Arabidopsis* seedlings. (B) Up-regulation of SOS1 expression in roots and shoots of wild type plants. (C) SOS1 expression in sos2-1 mutant seedlings. (D) SOS1 expression in sos3-1 mutant seedlings. The same RNA blots were hybridized successively with SOS1, RD29A and actin cDNA probes. Actin was used as loading control and RD29A as control for the stress treatments. C, control treatment.

Figure 7D:
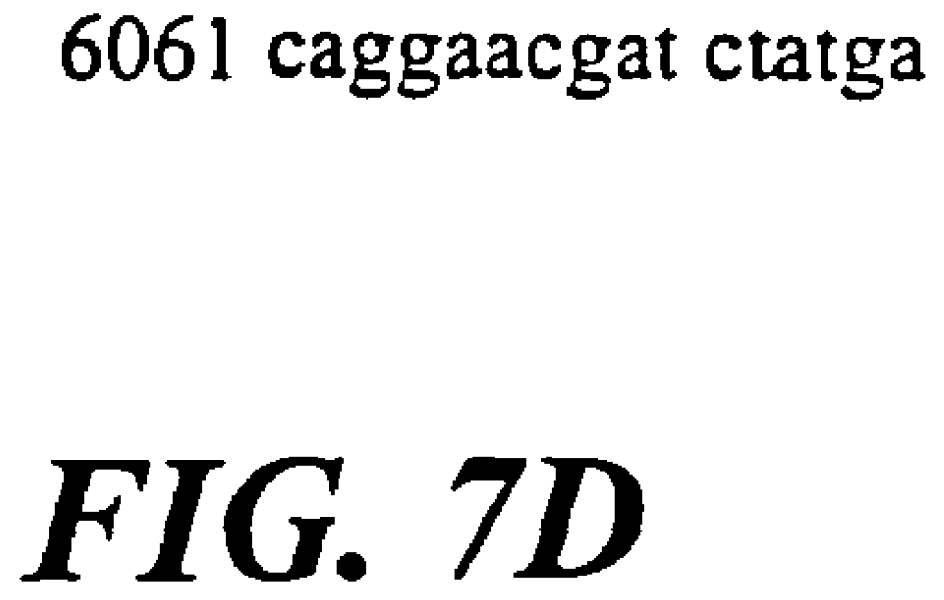

FIG. 7. Nucleotide sequence of the SOS1 gene, SEQ ID NO:1 (Genbank accession number AF256224). FIG. 7A shows nucleotides 1-1980 of SEQ ID NO:1, FIG. 7B shows nucleotides 1981-4020 of SEQ ID NO:1, FIG. 7C shows nucleotides 4021-6060 of SEQ ID NO:1, and FIG. 7D shows nucleotides 6061-6076 of SEQ TD NO:1.

DETAILED DESCRIPTION OF THE INVENTION

Figures 1A, 1B:
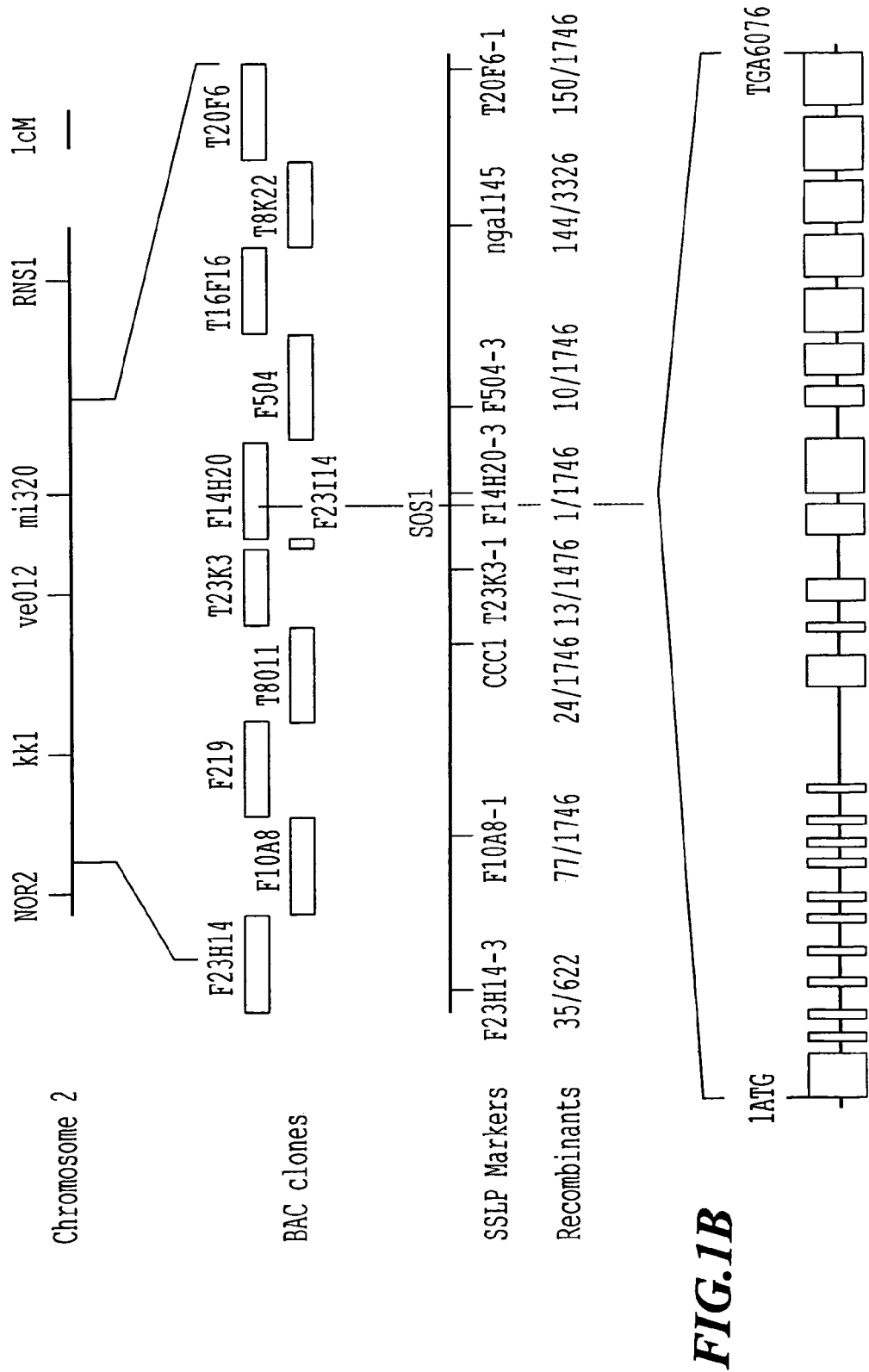
FIG. 1. Positional cloning of the SOS1 gene. (A) Physical mapping of SOS1. All the SSLP markers shown except ngal 145 were developed in this study based on sequence information of the bacterial artificial chromosomes (BACs). The BAC contig was assembled based on information available at publicly available databases, which are incorporated herein by reference. (B) Structure of the SOS1 gene. Positions are relative to the initiation codon. Filled boxes indicate the open reading frame and lines between boxes indicate introns.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); *Arabidopsis*, Meyerowitz et al, Eds., Cold Spring Harbor Laboratory Press, New York (1994) and the various references cited therein.

The term "plant" includes whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants. Preferred plants include rice, corn, wheat, cotton, peanut, and soybean.

Thus, in one embodiment of the present invention, the salt tolerance of a plant can be enhanced or increased by increasing the amount of protein available in the plant, preferably by the enhancement of the SOS1 gene in the plant.

Thus, one embodiment of the present invention are plant cells carrying the polynucleotides of the present invention, and preferably transgenic plants carrying the isolated polynucleotides of the present invention.

As used herein, the term "enhancement" means increasing the intracellular activity of one or more enzymes in a plant cell and/or plant which are encoded by the corresponding DNA. Enhancement can be achieved with the aid of various manipulations of the bacterial cell. In order to achieve enhancement, particularly over-expression, the number of copies of the corresponding gene can be increased, a strong promoter can be used, or the promoter- and regulation region or the ribosome binding site which is situated upstream of the structural gene can be mutated. Expression cassettes which are incorporated upstream of the structural gene act in the same manner. In addition, it is possible to increase expression by employing inducible promoters. A gene can also be used which encodes a corresponding enzyme with a high activity. Expression can also be improved by measures for extending the life of the mRNA. Furthermore, enzyme activity as a whole is increased by preventing the degradation of the enzyme. Moreover, these measures can optionally be combined in any desired manner. These and other methods for altering gene activity in a plant are known as described, for example, in Methods in Plant Molecular Biology, Maliga et al, Eds., Cold Spring Harbor Laboratory Press, New York (1995).

A gene can also be used which encodes a corresponding or variant enzyme with a high activity. Preferably the corresponding enzyme has a greater activity than the native form of the enzyme, more preferably at least in the range of 5, 10, 25% or 50% more activity, most preferably more than twice the activity of the native enzyme.

In the context of the present Application, a polynucleotide sequence is "homologous" with he sequence according to the invention if at least 70%, preferably at least 80%, most preferably at least 90% of its base composition and base sequence corresponds to the sequence according to the invention. According to the invention, a "homologous protein" is to be understood to comprise proteins which contain an amino acid sequence at least 70% of which, preferably at least 80% of which, most preferably at least 90% of which, corresponds to the amino acid sequence which is encoded by the SOS1 gene (SEQ ID No.1), wherein corresponds is to be understood to mean that the corresponding amino acids are either identical or are mutually homologous amino acids. The expression "homologous amino acids" denotes those which have corresponding properties, particularly with regard to their charge, hydrophobic character, steric properties, etc.

Homology, sequence similarity or sequence identity of nucleotide or amino acid sequences may be determined conventionally by using known software or computer programs such as the BesiFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The present invention also relates to polynucleotides which contain the complete gene with the polynucleotide sequence corresponding to SEQ ID No. 1 or fragments thereof, and which can be obtained by screening by means of the hybridization of a corresponding gene bank with a probe which contains the sequence of said polynucleotide corresponding to SEQ ID No. 1 or a fragment thereof, and isolation of said DNA sequence.

Polynucleotide sequences according to the invention are suitable as hybridization probes for RNA, cDNA and DNA, in order to isolate those cDNAs or genes which exhibit a high degree of similarity to the sequence of the SOS1 gene.

Polynucleotide sequences according to the invention are also suitable as primers for polymerase chain reaction (PCR) for the production of DNA which encodes an enzyme having activity of a $Na^+/H^+$ transporter.

Oligonucleotides such as these, which serve as probes or primers, can contain more than 30, preferably up to 30, more preferably up to 20, most preferably at least 15 successive nucleotides. Oligonucleotides with a length of at least 40 or 50 nucleotides are also suitable.

The term "isolated" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins which contain two or more amino acids which are bound via peptide bonds.

The polypeptides according to invention include polypeptides corresponding to SEQ ID No. 2, particularly those with the biological activity of a $Na^+/H^+$ transporter, and also includes those, at least 70% of which, preferably at least 80% of which, are homologous with the polypeptide corresponding to SEQ ID No. 2, and most preferably those which exhibit a homology of least 90% to 95% with the polypeptide corresponding to SEQ ID No. 2 and which have the cited activity.

The invention also relates to coding DNA sequences which result from SEQ ID No. 1 by degeneration of the genetic code. In the same manner, the invention further relates to DNA sequences which hybridize with SEQ ID No. 1 or with parts of SEQ ID No. 1. Moreover, one skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral. It is also known that changes at the N- and/or C-terminus of a protein do not substantially impair the function thereof, and may even stabilise said function.

In the same manner, the present invention also relates to DNA sequences which hybridize with SEQ ID No. 1 or with parts of SEQ ID No. 1. Finally, the present invention relates to DNA sequences which are produced by polymerase chain reaction (PCR) using oligonucleotide primers which result from SEQ ID No.1. Oligonucleotides of this type typically have a length of at least 15 nucleotides.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the Tm can be approximated from the equation of Meinkoth and Wahl, Anal. Biochem., 138:267-284 (1984): Tm=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

Thus, with the foregoing information, the skilled artisan can identify and isolated polynucleotides which are substantially similar to the present polynucleotides. In so isolating such a polynucleotide, the polynucleotide can be used as the present polynucleotide in, for example, increasing the salt tolerance of a plant.

One embodiment of the present invention is methods of screening for polynucleotides which have substantial homology to the polynucleotides of the present invention, preferably those polynucleotides encode a protein having $Na^+/H^+$ transporter activity.

The polynucleotide sequences of the present invention can be carried on one of more suitable plasmid vectors, as known in the art for plants or the like.

In one embodiment, it may be advantageous for propagating the polynucleotide to carry it in a bacterial or fungal strain with the appropriate vector suitable for the cell type. Common methods of propagating polynucleotides and producing proteins in these cell types are known in the art and are described, for example, in Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989).

SPECIFIC EMBODIMENTS OF THE INVENTION

Materials and Methods

Genetic Mapping sos1 mutant plants in the Columbia (Col) background were crossed to wild type plants of the Landsberg (Ler) ecotype. sos mutants were selected from the segregating F2 population by the root-bending assay (11). Genomic DNA from 1663 individual mutant F2 plants was analyzed for cosegregation with SSLP markers. For the fine mapping of SOS1, 7 SSLP markers were developed based on genomic sequences of the BAC clones at the top of chromosome 2. The primer pairs for the SSLP markers that are polymorphic between Col and Ler are as follows:

```
T20F6-1-F:     5'-GGATGATGATCGATTCGGAT-3'      (SEQ ID NO:5)

T20F6-1-R:     5'-ATCTGACTCATAGGATATCG-3'      (SEQ ID NO:6)

ngal 145-F:    5'-CCTTCACATCCAAAACCCAC-3'      (SEQ ID NO:7)

ngal 145-R:    5'-GCACATACCCACAACCAGAA-3'      (SEQ ID NO:8)

F504-3-F:      5'-GAATGTTTTGAAGGATATCTCAG-3'   (SEQ ID NO:9)

F504-3-R:      5'-GAAAAATGGAGCACGAAATAAGC-3'   (SEQ ID NO:10)

F14H20-3-F:    5'-CCCGAGATTAATACACAATC-3'      (SEQ ID NO:11)

F14H20-3-R:    5'-GCAGATTATGTAATTGTGACC-3'     (SEQ ID NO:12)

T23K3-1-F:     5'-TCGTGTTTACCGGGTCGGAT-3'      (SEQ ID NO:13)

T23K3-1-R:     5'-TGATGAGAATCTTAGCGAGC-3'      (SEQ ID NO:14)

CCC-1-F:       5'-TGGTAAGACCAAATTACACTC-3'     (SEQ ID NO:15)

CCC-I-R:       5'-CGTAATTAAAATGTGTTAAACCG-3'   (SEQ ID NO:16)

F10A8-1-F:     5'-AACCGCATAGTACAATGCAG-3'      (SEQ ID NO:17)

F10A8-1-R:     5'-CGGTAAAGATCAACTAATAACG-3'    (SEQ ID NO:18)

F23H14-3-F:    5'-AACGGAAACGGCAACTAGAC-3'      (SEQ ID NO:19)

F23H14-3-R:    5'-ACCCTAAATGTTTCGATTCG-3'      (SEQ ID NO:20)
```

DNA Sequencing

To determine the nucleotide sequence of SOS1 gene in sos1 mutant alleles, synthetic oligonucleotide primers were made that would enable sequencing of the entire gene. Overlapping fragments encompassing the entire SOS1 gene were PCR amplified by using these primers. The amplified products were sequenced on both strands. To avoid errors due to PCR, three independent PCR samples were mixed and batch sequenced.

Isolation of cDNA cDNA containing the complete SOS1 open reading frame was obtained by reverse transcription (RT)-PCR amplification. RNA, from salt-treated Col wild type plants was used as template for the RT-PCR. Three overlapping cDNA fragments obtained from RT-PCR were mixed as the template to amplify a full length cDNA which was then cloned into pCR-Blunt II-TOPO Vector (Invitrogen).

Plant Transformation and Complementation Test

SOS1 cDNA containing the entire open reading frame was cloned into the XbaI and SacI sites of pBI121. The construct was introduced into *Agrobacterium* GV3101 strain, and the resulting bacteria were used to transform sos1-1 mutant plants by vacuum infiltration (18). Kanamycin resistant T2 transgenic plants were selected and subjected to complementation tests on MS agar medium supplemented with 100 mM NaCl.

RNA Analysis

*Arabidopsis* seedlings were grown on MS agar medium under continuous light (11). Ten-day-old seedlings were used for different treatments. For salt treatment, the seedlings were transferred onto a Whatman filter paper soaked with 3 mM NaCl and treated for 5 h. For ABA treatment, the seedlings were sprayed with 10 μM ABA and kept for 3 h. For cold treatment, the seedlings on MS agar medium were incubated at 0° C. for 24 h. To determine gene expression in root and shoot separately, seedlings were grown on agar surface in vertical plates for 10, days, treated with NaCl by immersing the roots in MS nutrient solution supplemented with 200 mM NaCl for 6 h. RNA extraction and Northern analysis were carried out as described (13).

Results

Positional Cloning of SOS1

Figure 2:
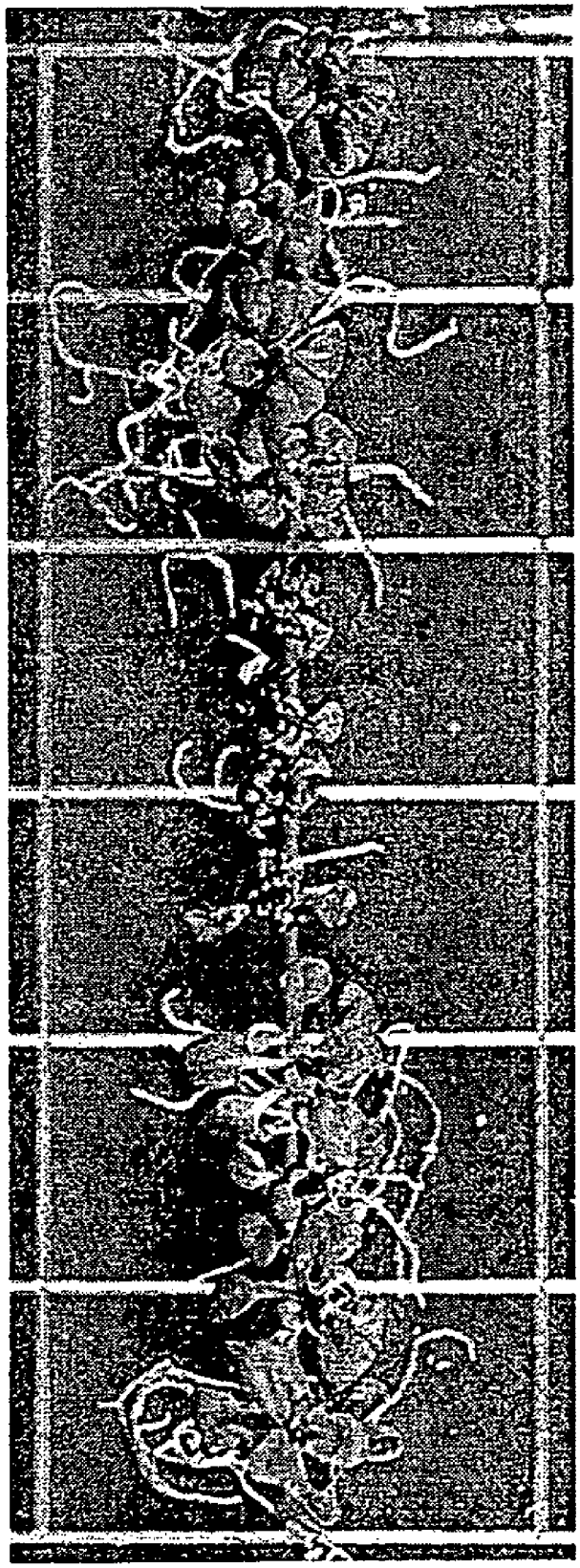
FIG. 2. Complementation of sos1 by 35S-SOS1. Seven-day-old seedlings grown on MS agar medium were transferred to MS medium supplemented with 100 mM NaCl. The picture was taken after 10 days of treatment on the NaCl medium. Left, wild type plants (WT). Center, sos1-1 mutant plants. Right, transgenic sos1-1 plants containing the wild type SOS1 gene under control of the CaMV 35S promoter. These plants did not show any difference when grown on MS medium without supplementation of NaCl.

By examining several PCR based molecular markers, we found that the SSLP marker ngal 145 near the top of chromosome 2 is closely linked to the sos1 mutation. Seven new SSLP markers were then developed based on the genomic, sequence of BAC clones at the top of chromosome 2. Fine mapping using these markers delimited SOS1 to about 70 kb region between the molecular markers T23K3-1 and F14H20-3 (FIG. 1A). Candidate genes in this region were amplified from soil mutants and sequenced. The sequence analysis revealed that a putative gene, F14H20.5, contains a 2 bp deletion in the sos1-13 mutant allele generated by fast neutron bombardment. Further analyses showed that all sos1 alleles contain mutations in this putative gene and each mutation causes a change in the amino acid sequence (Table 1). Furthermore, expression of this candidate gene under control of the CaMV 35S promoter complemented the salt-hypersensitive phenotype of sos1-1 mutant plants (FIG. 2). When sos1-1 mutant seedlings were treated with 100 mM NaCl, their growth was arrested. In these mutant plants, older leaves became chlorotic while young leaves became dark in color. In contrast, sos1-1 mutant plants containing the 35S-SOS1 transgene could grow, and remained green under 100 mM NaCl treatment, as did the wild type plants. Based on these results, we conclude that this putative gene is SOS1.

SOS1 Encodes a Putative Na$^+$/H$^+$ Antiporter

Figure 5:
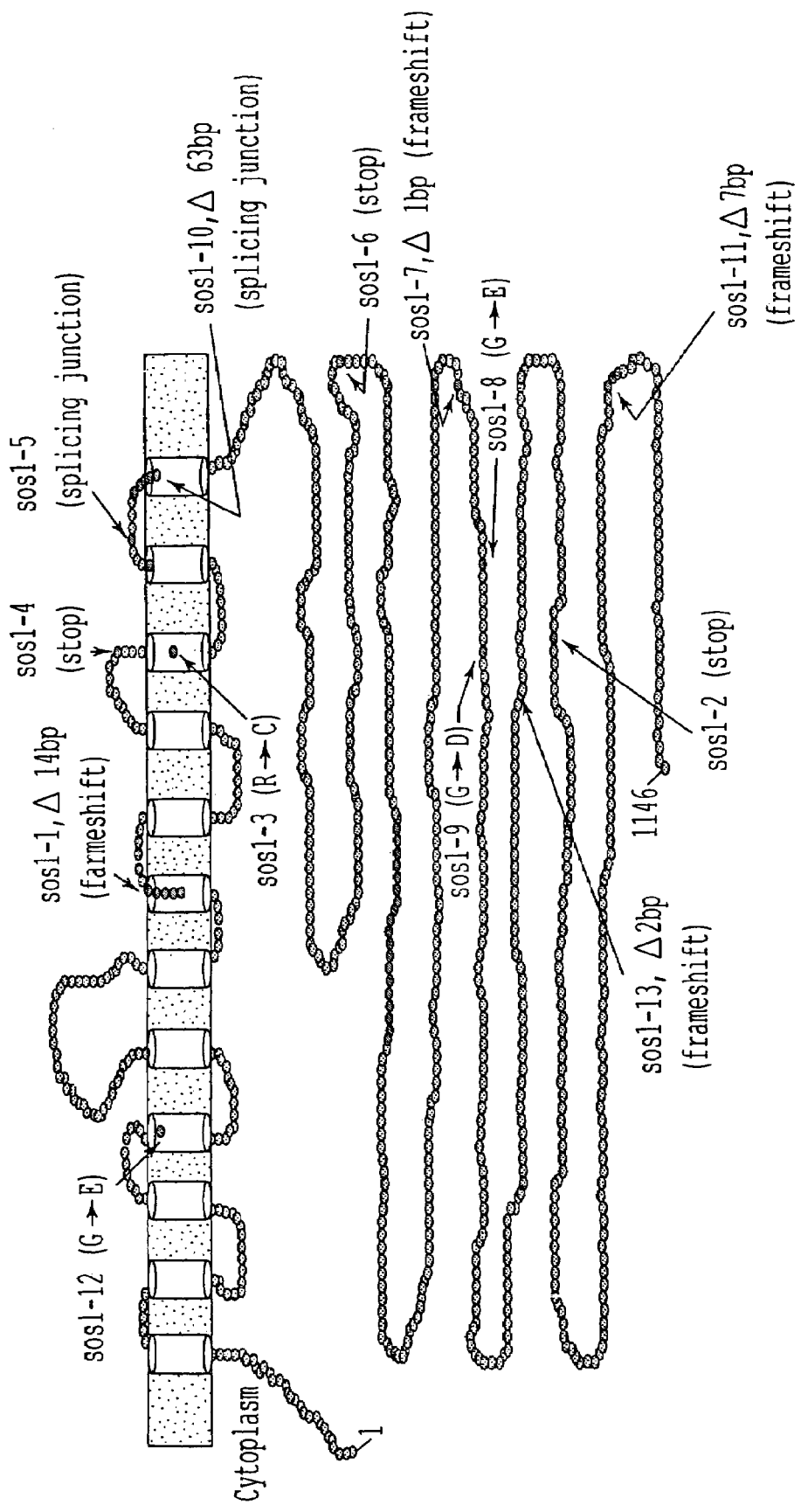
FIG. 5. Diagrammatic representation of SOS1 structure. The diagram was drawn based on the prediction of hydrophobicity profile of SOS1. Putative transmembrane helices are shown as cylinders. The positions of mutations in sos1 alleles are indicated.
Figure 8:
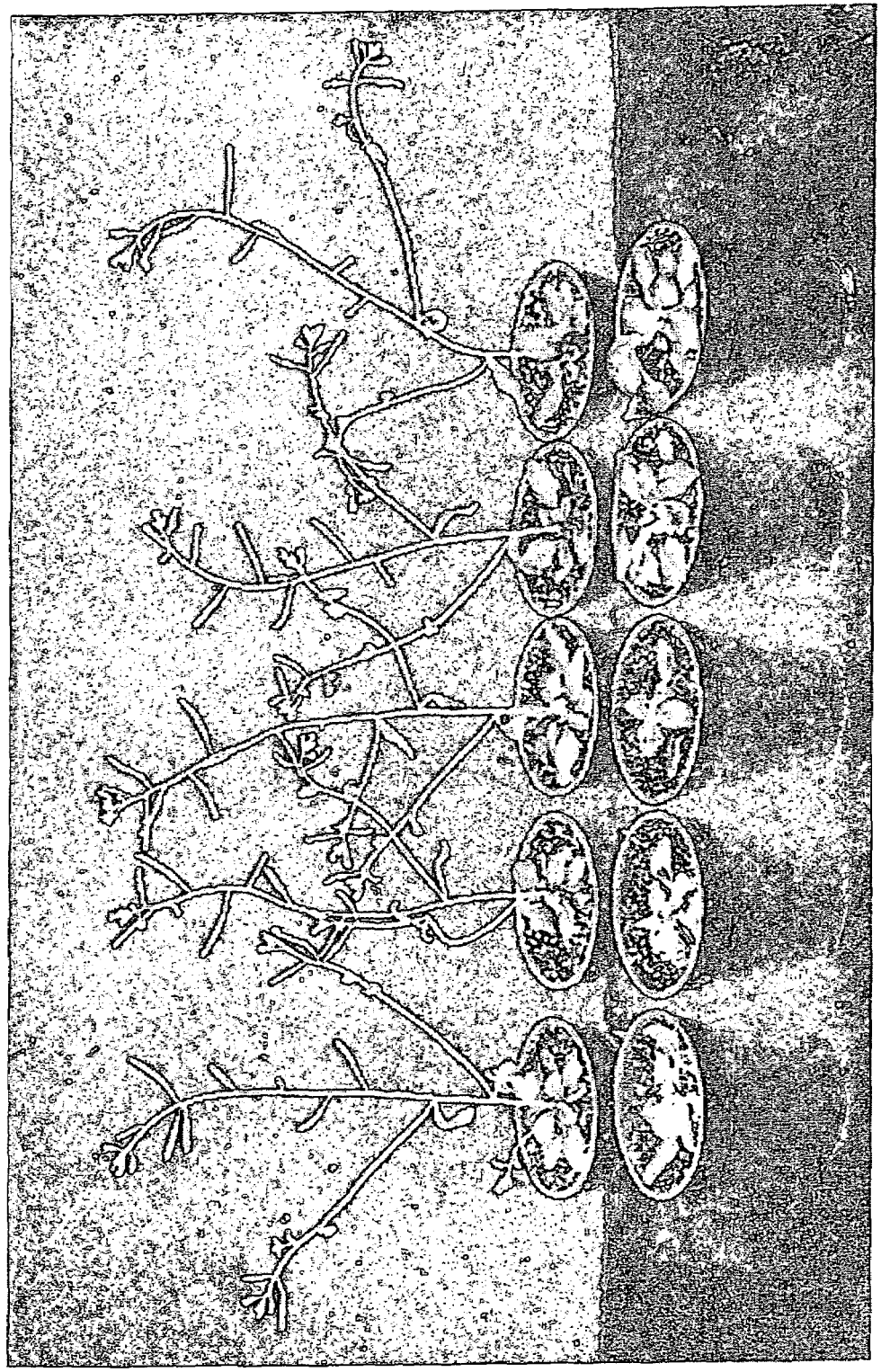
FIG. 8. Overexpression of SOS1 improves salt tolerance of *Arabidopsis* plants. Transformed plants overexpressing SOS1 and control plants that were transformed with a vector only were compared for their salt tolerance. All plants were grown in soil on a long-day cycle (16 hours light, 8 hours dark). The first 13 days after germination the plants were watered with a diluted nutrient solution (⅛ MS) as needed. Starting on the 14th day, this solution was supplemented with NaCl. The supplementations consisted of four increasingly higher concentrations (50 mM, 100 mM, 150 mM, and 200 mM) of NaCl. The plants were treated for four days at each concentration, for a total of 16 days. On the 16th day the picture shown in the figure was taken.

The SOS1 open reading frame was determined by sequencing several overlapping cDNAs obtained from young *Arabidopsis* seedlings by reverse transcriptase polymerase chain reaction. Comparison with the genomic sequence revealed that SOS1 has 22 introns and 23 exons (FIG. 1B). SOS1 is predicted to encode a polypeptide of 1146 amino acid residues (FIG. 3A) with a theoretical molecular mass of 127 kDa. Hydrophobicity plot analysis showed that the N-terminal portion of SOS1 is highly hydrophobic and has 12 predicted transmembrane domains (FIG. 3B). Database searches revealed substantial similarities between the transmembrane region of SOS1 and Na$^+$/H$^+$ antiporters of animal or microbial origins (FIG. 4A). Over a stretch of 342 amino acid residues (113-443), SOS1 has 26% identity and 45% similarity with NHE1 from Chinese hamster (19). The highest sequence similarities for SOS1 are with the "eucaryotic" type Na$^+$/H$^+$ antiporters from bacteria, of which only NhaP from *Pseudomonas aeruginosa* has been functionally characterized (20). SOS1 exhibits 31% identity and 48% similarity with the NhaP sequence over a stretch of 289 amino acids (131-408 in SOS1). The C-terminal portion of SOS1 is hydrophilic and predicted to reside in the cytoplasm (FIG. 5). The long hydrophilic carboxyl-terminal tail makes SOS1 the largest Na$^+$/H$^+$ antiporter sequence known to date. No similarities were Found between the SOS1 tail region and other amino acid sequences in the GenBank database.

Phylogenetic analysis showed that SOS1 clusters with plasma membrane Na$^+$/H$^+$ antiporters such as SOD2, NHa1, NhaA and NhaP (FIG. 4B). SOD2 and NHA1 function on the plasma membrane of *S. pombe* and *S. cerevisiae*, respectively, to export Na$^+$ from cytosol to the extracellular space (21, 22, 23). NhaA and NhaP are Na$^+$/H$^+$ antiporters that function in Na$^+$ efflux in *E. coli* and *P. aeriuginosa*, respectively (20, 24). SOS1 is more distantly related to a cluster of orgaruellar Na$^+$/H$^+$ antiporters such as AtNHX1, NHX1 or NHE6 (FIG. 4B). AtNHX1 functions on the tonoplast to compartmentalize Na$^+$ into the vacuole of *Arabidopsis* cells (6, 7). NHX1 plays a role in transporting Na$^+$ to the yeast prevacuolar compartment (25, 26). The animal Na$^+$/H$^+$ antiporter NHE6 has been reported to have a mitochondrial localization (2'7). SOS1 does not cluster with plasma membrane Na$^+$/H$^+$ antiporters from animals, which function in mediating Na$^+$ influx (28). These results suggest that SOS1 is distinct from vacuolar Na$^+$/H$^+$ antiporters, and may function at plant cell plasma membrane to mediate Na$^+$ efflux.

Analysis of sos1 Mutant Alleles Reveals Several Residues and Regions Essential for SOS1 Function The SOS1 gene was amplified from thirty-two independent sos1 mutant lines (13) and sequenced to determine the molecular basis of each mutation. Several mutant lines were found to harbor identical mutations (Table 1). Five of the fast neutron alleles result in relatively large deletions and were not assigned specific allele designations because the boundaries of the deletions are not known. Analysis of the various sos1 mutations reveals several amino acid residues and regions essential for SOS1 function. The sos1-3 and sos1-12 alleles contain single amino acid substitutions in the membrane spanning region (FIG. 5). Both mutations affect residues that are conserved in all antiporters (FIG. 4A) and presumably abolish SOS1 antiport activity. Two other single amino acid substitution mutations (i.e. sos1-8 and sos1-9) one found in the hydrophilic tail region (FIG. 5). The sos1-10 allele was obtained from T-DNA mutagenesis and contains a 7-bp deletion that causes a frameshift that truncates the last 40 amino acids from the C-terminus of SOS1 (FIG. 5). Similarly, sos1-2 and sos1-6 mutations also truncate the cytoplasmic tail of SOS1 (FIG. 5). These and other mutations that do not affect the transmembrane region reveal an essential role of the tail region for SOS1 function. Like the hydrophilic tail of animal NHE1 antioporters (29), the tail of SOS1 may interact with various regulators of antiport activity. As such, these mutations likely disrupt interaction between SOS1 and its regulators.

SOS1 Expression Is Up-regulated Specifically by Salt Stress

To examine the expression of SOS1 gene under stresses, RNA gel blot analysis was performed, SOS1 mRNA was detected without stress treatment but was significantly up-regulated by salt stress (FIG. 6A). Consistent with its specific role in Na$^+$ tolerance, SOS1 gene expression was not up-regulated by cold stress or ABA (FIG. 6A). In comparison, the RD29A gene was induced by ABA, cold as well as salt stresses. SOS1 mRNA was more abundant in roots than in shoots. In both roots and shoots, SOS1 expression was up-regulated by NaCl stress (FIG. 6B).

SOS1 Up-Regulation Is Controlled by the SOS3/SOS2 Pathway

To determine whether NaCl up-regulation of SOS1 is under control of the SOS3/SOS2 regulatory pathway, SOS1 expression in sos2-1 and sos3-1 mutant plants was analyzed. In the sos2 mutant. SOS1 was up-regulated by NaCl stress in the root but not in the shoot (FIG. 6C). In sos3 plants, no SOS1 up-regulation was seen in either the root or shoot (FIG. 6D). These results show that SOS1 expression is regulated at least in part by the SOS31SOS2 pathway.

Discussion

SOS1 is a genetic locus that was previously identified as essential for plant salt tolerance (11). Mutations in SOS1 render *Arabidopsis* plants extremely sensitive to high Na$^+$ or low K$^+$ environment (11, 13). In order to understand how the SOS1 gene functions in salt tolerance, it was necessary to clone this gene. Even though several sos1 mutant lines were recovered from a T-DNA insertion population, the T-DNA did not co-segregate with the sos1 mutant phenotype (13). Therefore, a map-based strategy had to be utilized to clone the SOS1 gene. Fine genetic mapping narrowed the search of SOS1 to a very short region of chromosome 2. The fine mapping of SOS1 was made possible by the several molecular markers we have developed and the large number of recombinant chromosomes examined. Several candidate genes in the region where SOS1 is mapped were sequenced to identify the sos1 mutation. One of the candidate genes was found to contain a mutation in every sos1 mutant allele. Further confirmation that this candidate is indeed SOS1, came from genetic complementation test.

The SOS1 protein is predicted to have 12 transmembrane domains in its N-terminal part. Throughout this transmembrane region, SOS1 shows substantial sequence similarities with Na$^+$/H+antiporters from microbes and animals. The sequence similarities combined with the Na$^+$ hypersensitive phenotype of sos1 mutant plants strongly indicate that SOS1 is a Na$^+$/H$^+$ antiporter. Phylogenetic analysis showed that SOS1 is more closely related to plasma membrane Na$^+$/H$^+$ antiporters from microorganisms than to the vacuolar antiporters from either plants or fungi. This suggests that SOS1 is a plasma membrane Na$^+$/H$^+$ antiporter in *Arabidopsis*, As such, SOS1 is expected to function in exporting Na$^+$ from the cytosol to the extracellular space, to prevent rapid accumulation of Na$^+$ in the cytoplasm.

SOS1 is predicted to have a cytoplasmic tail of approximately 700 amino acids in length. Sequence analysis of the multitude of sos1 mutant alleles revealed that both the tail and transmembrane regions of SOS1 are necessary for its function in plant salt tolerance. The sos1-3, sos1-8, sos1-9 and sos1-12 mutations each causes a single amino acid substitution in the SOS1 protein. Two of these substitutions occur in the transmembrane region and the other two in the tail. These four residues are clearly critical for SOS1 function. The data presented herein on the sos1 mutant lesions provide a wealth of information that will be valuable for detailed structure-function analysis.

SOS1 gene expression is up-regulated by NaCl stress. This is consistent with its role in $Na^+$ tolerance. It has been known that NaCl stress also up-regulates the expression of genes encoding plasma membrane $H^+$-ATPases (30). Increased $H^+$-ATPase expression would provide a greater proton motive force that is necessary for elevated $Na^+/H^+$ antiporter activity.

The SOS3 calcium sensor physically interacts with the SOS2 protein kinase (17). In the presence of calcium, SOS3 activates SOS2 kinase activity. The SOS3-SOS2 kinase complex represents a regulatory pathway that specifically controls $Na^+$ and $K^+$ homeostasis and plant salt tolerance. Results presented in this paper suggest that one output of this pathway is the up-regulation of SOS1 expression under NaCl stress. The sos3 mutation abolishes SOS1 up-regulation in both the root and shoot. In the sos2 mutant, SOS1 up-regulation in the shoot but not in root was disrupted. The fact that SOS1 expression is still up-regulated in the root of sos1 mutant indicates that there may be a functionally redundant root-specific SOS2-like kinase(s). The regulation of SOS1 gene expression by the SOS2/SOS3 pathway is consistent with previous genetic evidence suggesting that SOS1 functions in the same pathway as SOS2 and SOS3 (12, 13).

SOS1 is essential for the homeostasis of both $Na^+$ and $K^+$. Under NaCl stress, sos1 mutant plants accumulate less $Na^+$ as well as less $K^+$ (11, 31). SOS1 gene expression is concentrated in cells surrounding the xylem, suggesting that SOS1 may function in loading $Na^+$ into the xylem for long distance transport (our unpublished data). A xylem loading function of SOS1 would be consistent with sos1 mutant plants accumulating less $Na^+$. Preferential expression of SOS1 at the symplast/xylem boundary would also help explain the $K^+$ transport defect of sos1 mutant plants. It is well known that $H^+$ and $Na^+$ transport is closely linked at the xylem/symplast interface (32). The effect of SOS1 on $K^+$ transport might be through its effect on $H^+$ gradient across the cell membrane of stellar cells. For example, a $K^+$-$H^+$ symporter activity could be coupled with SOS1 via $H^+$ cycling and such a symporter may be required for high affinity $K^+$ transport into the xylem. It is also possible that a $K^+/Na^+$ symporter is coupled with SOS1 via $Na^+$ cycling.

TABLE 1

Molecular basis of sos1 mutations.

| Mutant line | Allele | Mutagen | Nucleotide change | Protein change |
| --- | --- | --- | --- | --- |
| ssr1, Icss-3, Icss1-18 | sos1-1 | EMS | ▲14 bp, 1330-1343 | frameshift |
| ss1-6, ss3-13 | sos1-2 | EMS | C5410-T | stop |
| ss1-16, Icss1-24 | sos1-3 | EMS | C2520-T | Arg-365-Cys |
| IIcss1-13, IIcss1-22 | sos1-4 | EMS | G-2480-A | stop |
| Icss1-10 | sos1-5 | EMS | G2766-A | splicing junction |
| Icss1-25 | sos1-6 | EMS | G3652-A | stop |
| IIcss1-59, css1-61 | sos1-7 | EMS | ▲1 bp, 4539 | frameshift |
| Icss2-21 | sos1-8 | EMS | G-4594-A | Gly-777-Glu |
| Icss2-7 | sos1-9 | EMS | G-4615-A | Gly-784 = Asp |
| tss2-1, p2901-3503 2-1 | sos1-10 | T-DNA | ▲63 bp, 2792-2854 | splicing junction |
| P800 1-2, p800 1-3 | sos1-11 | T-DNA | ▲7 bp, 5953-5959 | frameshift |
| FN50css2-3, FN50css3-22, FN75cssl-24, FN75css1-14, FN75css3-18 | sos1-12 | fast neutron | G-668-A | Gly-136-Glu |
| FN50css2-9, FN75css1-22, FN75css1-23 | sos1-13 | fast neutron | ▲2 bp, 5149-5150 | frameshift |
| FN50css1-8, FN50css3-3, FN75css1-17, B46, B47 | | fast neutron | Whole gene deletions | |

REFERENCES

1. Niu, X., Bressan R. A., Hasegawa, P, M. & Pardo, J. M. (1995) *Plant Physiol.* 109, 735-742.
2. Jacoby, B. (1999) in Handbook of Plant and Crop Stress. ed. Pessarakli M. (Marcel Dekker, New York), pp 97-123.
3. Rubio, F., Gassman, W. & Schroeder, J. I. (1995) *Science* 270, 1660-1663.
4. Schachtman, D. P., Kumar, R., Schroeder, J. I. & Marsh, E. L. (1997) *Proc. Natl. Acad. Sci. U.S.A.* 94, 11079-11084.
5. Amtmann, A. & Sanders, D. (1998) *Adv. Bot Res.* 29, 76-112.
6. Gaxiola R. A., Rao, R., Sherman, A., Grisafi, P., Alper, S. L. & Fink, G. R. (1999) *Proc. Natl. Acad. Sci.* U.S.A. 96, 1480-1485.
7. Apse, M. P., Aharon, G. S., Snedden, W. A. & Blumwald E. (1999) *Science* 285, 1256-1258.
8. Schachtman, D. P. & Liu, W. (1999) *Trends Plant Sci.* 4, 281-287.
9. Haro, R., Garciadeblas, B. & Rodriguez-Navarro, A. (1991) *FEBS Lett.* 291, 189-191.
10. Jia, Z., McCullough, N., Martel, R., Hemmingsen, S. & Young, P. G. (1992) *EMBO J.* 11, 1631-1640.
11. Wu, S.-J., Lei, D. & Zhu, J.-K. (1996) *Plant Cell* 8, 617-627.
12. Liu, J. & Zhu, J.-K. (1997), *Proc. Natl. Acad. Sci. U.S.A.* 94, 14960-14964.
13. Zhu, J. K., Liu, J. & Xiong, L. (1998) *Plant Cell* 10, 1181-1191.
14. Liu, J. & Zhu, J.-K. (1998) *Science* 280, 1943-1945.
15. Mendoza, I., Rubio, F., Rodriguez-Navarro, A. & Pardo, J. M. (1994) *J. Biol. Chem.* 269, 8792-8796.
16. Liu, J., Ishitani, M., Halfter, U., Kim, C.-S. & Zhu, J.-K. (2000) *Proc. Natl. Acad. Sci. USA* (in press).
17. Halfter, U., Ishitani, M-. & Zhu, J.-K. (2000) *Proc. Natl. Acad Sci, U.S.A.* (in press).
18. Bechtold, N., Ellis, J. & Pelletier, G. (1993) *CR Acad. Sci.* (Paris) 316, 1194-1199.

19. Counillon, L. & Pouyseegur, J. (1993) *Biochim. Biophys. Acta* 1172, 343-345
20. Utsugi, 3., Inaba, K., Kuroda, T., Tsuda, M. & Tsuchiya, T. (1998) *Biochim Biophys. Acta* 1398, 330-334,
21. Hahnenberger, K. M., Jia, Z. & Young, P. C. (1996) *Proc. Natl. Acad. Sci. USA.* 93, 5031-5036.
22. Dibrov, P., Smith, J. J., Young, P. G. & Fliegel, L. (1997) *FEBS Lett.* 405, 119-124.
23. Prior, C., Potier, S., Souciet, J. L.; & Sychrova, H. (1996) *FEBS Lett.* 387, 89-93.
24. Padan, E., Maisler, N., Taglicht, D., Karpel, R. & Schuldiner, S. (1989) *J. Biol. Chem.* 264, 20297-20302.
25. Nass, R., Cunningham, K. W. & Rao, R. (1997) *J. Biol. Chem.* 272, 26143-26152.
26. Nass, R. & Rao, R. (1998) *J. Biol. Chem.* 273, 21054-21060.
27. Numata, M., Petrecca, K., Lake, N. & Orlowski, J. (1998) *J. Biol. Chem.* 273, 6951-5959.
28. Orlowski, J. & Grinstein, S. (1997) *J. Biol. Chem.* 272, 22373-22376.
29. Silva, N. L., Haworth, R. S., Singh, D. & Fliegel L. (1995) *Biochem.* 34, 10412-10420.
30. Niu, X., Narasimhan, M. L., Salzman, R. A., Bressan, R. A. & Hasegawa, P. M. (1993) *Plant Physiol.* 143, 713-718.
31. Ding, L. & Zhu, J.-K. (1997) *Plant Physiol.* 113, 795-799.
32. Lacan, D. & Durand, M. (1996) *Plant Physiol.* 110, 705-711.

The invention claimed is:

1. A method of increasing the salt tolerance of a plant in need thereof, comprising increasing the expression of a polynucleotide encoding a polypeptide that is at least 95% identical to the amino acid sequence of SEQ ID NO: 2, wherein said polypeptide has Na$^+$/H$^+$ antiporter activity, in said plant as compared to the expression of said polynucleotide in the wild-type of said plant, and wherein said increasing the expression is by either increasing the copy number of said polynucleotide as compared to the wild-type plant or by replacing the native promoter of said polynucleotide with a stronger promoter.

2. The method of claim 1, wherein said polynucleotide comprises the sequence of SEQ ID NO: 1.

3. The method of claim 1, wherein said polynucleotide encodes the polypeptide of SEQ ID NO: 2.

4. The method of claim 1, wherein said plant is *Arabidopsis thaliana*.

5. The method of claim 1, wherein said plant is selected from the group consisting of wheat, corn, peanut cotton, oat, and soybean plant.

6. The method of claim 1, wherein said increasing the expression comprises increasing the copy number of said polynucleotide as compared to the wild-type plant.

7. The method of claim 1, wherein said increasing the expression comprises replacing the native promoter of said polynucleotide with a stronger promoter.

8. The method of claim 1, wherein said plant is a monocotyledonous plant.

9. The method of claim 1, wherein said plant is a dicotyledonous plant.

10. The method of claim 1, wherein said increasing the expression is in a plant organ.

11. The method of claim 10, wherein said plant organ is selected from the group consisting of leaves, stems, and roots.

12. The method of claim 1, wherein said increasing the expression is in the whole plant.

13. The method of claim 1, wherein said increasing the expression is in the seeds of said plant.

* * * * *